(12) United States Patent
Chin

(10) Patent No.: US 10,925,490 B2
(45) Date of Patent: *Feb. 23, 2021

(54) MITIGATING EXCESSIVE WAKEUPS IN LEADLESS DUAL-CHAMBER PACING SYSTEMS AND OTHER IMD SYSTEMS

(71) Applicant: Pacesetter, Inc., Sylmar, CA (US)

(72) Inventor: Donald Chin, Palo Alto, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/423,152

(22) Filed: May 27, 2019

(65) Prior Publication Data

US 2019/0296834 A1    Sep. 26, 2019

Related U.S. Application Data

(63) Continuation of application No. 15/413,820, filed on Jan. 24, 2017, now Pat. No. 10,342,429.

(51) Int. Cl.
*A61B 5/00* (2006.01)
*H04B 13/00* (2006.01)
(Continued)

(52) U.S. Cl.
CPC .............. *A61B 5/0024* (2013.01); *A61N 1/36* (2013.01); *A61N 1/3756* (2013.01);
(Continued)

(58) Field of Classification Search
CPC .... A61B 5/0024; A61N 1/36; A61N 1/37205; A61N 1/37376; A61N 1/3756; A61N 1/37512; A61N 1/37518; H04B 13/005
See application file for complete search history.

(56) References Cited

U.S. PATENT DOCUMENTS

2003/0187484 A1* 10/2003 Davis ................. A61N 1/37211
                                                                    607/60
2010/0023085 A1   1/2010 Wu et al.
(Continued)

OTHER PUBLICATIONS

Non-Final Office Action dated Jul. 26, 2018 for U.S. Appl. No. 15/413,820 24 pages.
(Continued)

*Primary Examiner* — Amine Benlagsir
(74) *Attorney, Agent, or Firm* — The Small Patent Law Group LLC; Dean D. Small

(57) ABSTRACT

Techniques for use with an implantable medical device (IMD) reduce how often a first receiver of the IMD wakes up a second receiver thereof to reduce power consumption. A received message and/or a channel over which messages can be received is/are examined, and a value is adjusted based on results thereof. After being adjusted, the value is compared to a first threshold if the IMD is in a normal state, or compared to a second threshold if the IMD is in a noise state. If in the normal state, there is a determination whether to stay in the normal state or switch to the noise state. If in the noise state, there is a determination whether to stay in the noise state or switch to the normal state. At least the second receiver is temporarily put to sleep, if the IMD is maintained in or switched to the noise state.

28 Claims, 10 Drawing Sheets

(51) Int. Cl.
  *A61N 1/36*   (2006.01)
  *A61N 1/372*  (2006.01)
  *A61N 1/375*  (2006.01)

(52) U.S. Cl.
  CPC ..... *A61N 1/37205* (2013.01); *A61N 1/37276* (2013.01); *H04B 13/005* (2013.01); *A61N 1/37288* (2013.01); *A61N 1/37512* (2017.08); *A61N 1/37518* (2017.08)

(56) References Cited

U.S. PATENT DOCUMENTS

| | | |
|---|---|---|
| 2012/0071098 A1 | 3/2012 | Chebbo et al. |
| 2016/0121128 A1 | 5/2016 | Fishier et al. |
| 2016/0121129 A1 | 5/2016 | Persson et al. |
| 2016/0213937 A1* | 7/2016 | Reinke ............... A61N 1/37288 |
| 2017/0312530 A1* | 11/2017 | Schilling ................ H04L 67/12 |

OTHER PUBLICATIONS

Notice of Allowance dated Mar. 4, 2019 for U.S. Appl. No. 15/413,820 15 pages.

\* cited by examiner

MITIGATING EXCESSIVE WAKEUPS IN LEADLESS DUAL-CHAMBER PACING SYSTEMS AND OTHER IMD SYSTEMS

PRIORITY CLAIM

The present application is a continuation of U.S. patent application Ser. No. 15/413,820, filed Jan. 24, 2017, entitled "MITIGATING EXCESSIVE WAKEUPS IN LEADLESS DUAL-CHAMBER PACING SYSTEMS AND OTHER IMD SYSTEMS. The patent application identified above is incorporated here by reference in its entirety to provide continuity of disclosure.

FIELD OF TECHNOLOGY

Embodiments described herein generally relate to methods and systems for communication between implantable medical devices, or communicating between a non-implantable device and an implantable medical device.

BACKGROUND

The longevity of an implantable medical device (IMD) that is powered by a battery is dependent upon how much power is consumed by electronics of the device. Such electronics can be used, e.g., for pacing or delivering other types of stimulation, sensing or otherwise collecting information, as well as for communicating within another implantable device or a non-implantable device. Accordingly, power may be consumed when pacing or delivering other types of stimulation, collecting information, as well as when communicating. It would be beneficial to reduce power consumption in order to increase the longevity of an IMD.

SUMMARY

Implantable medical devices (IMDs) including a first receiver and a second receiver, and methods for use therewith are described herein. Such an IMD can be a leadless pacemaker (LP), but is not limited thereto. Certain embodiments of the present technology reduce how often the first receiver of the IMD wakes up the second receiver and thereby reduces how much power is consumed by the second receiver. Such a method can include examining a received message and/or a channel over which messages can be received, and selectively adjusting a value, indicative of a characteristic of messages received over time and/or indicative of a characteristic over time of the channel over which messages can be received, based on results of examining the received message and/or channel. In accordance with certain embodiments, an amount by which the value is selectively adjusted is different depending upon whether the IMD is in the normal state or the noise state. Additionally, or alternatively, an amount by which the value is selectively adjusted can be different depending upon whether the value is being increased or decreased.

After the value is adjusted, the value is compared to a first threshold if the IMD is in a normal state, or the value is compared to a second threshold if the IMD is in a noise state. If the IMD is in the normal state, there is a determination whether to maintain the IMD in the normal state or switch the IMD to the noise state, based on results of the value being compared to the first threshold. If the IMD is in the noise state, there is determination whether to maintain the IMD in the noise state or switch the IMD to the normal state, based on results of the value being compared to the second threshold. At least the second receiver is put to sleep for a sleep period, if the IMD is maintained in or switched to the noise state. The first receiver can also be put to sleep for the sleep period. During the sleep period, there may be no examining of any received messages. In accordance with certain embodiments, the sleep period is selectively increased or decreased based on the results of the received message being examined. Where the IMD is a pacing device, such as an LP, the IMD may pace in accordance with a safe pacing mode when the second receiver is sleeping.

In accordance with certain embodiments, prior to a received message being examined, the first receiver receives at least a portion of the message, and in response thereto, the first receiver wakes up the second receiver so that the second receiver, after being woken up by the first receiver, can examine the received message.

In accordance with specific embodiments, examining a received message involves determining whether the received message is valid or invalid, and the characteristic of messages received over time is an extent that valid or invalid message were received over time. In such embodiments, the value, which is indicative of the extent that valid or invalid messages were received over time, is adjusted based on results of the determining whether the received message was valid or invalid. In some such embodiments, the received message is processed if the received message was valid and the IMD is maintained or switched to the normal state, and the received message is not processed if the IMD is maintained or switched to the noise state. In accordance with specific embodiments, the value is an invalidity value indicative of the extent of invalid messages received over time, and adjusting the value includes decreasing the invalidity value if the received message is valid, or increasing the invalidity value if the received message is invalid. In accordance with other embodiments, the value is a validity value indicative of the extent of valid messages received over time, and adjusting the value includes increasing the validity value if the received message is valid, or decreasing the validity value if the received message is invalid.

In accordance with specific embodiments, examining a received message involves determining whether the received message was received in the presence or absence of excessive noise, and the characteristic of messages received over time is an extent that excessive noise was present or absent when messages were received over time. In such embodiments, the value, which is indicative of the extent that excessive noise was present or absent when messages were received over time, is adjusted based on results of the determining whether the received message was received in the presence or absence of excessive noise. In accordance with specific embodiments, examining the channel over which messages can be received involves determining whether excessive noise was present or absent in the channel over which messages can be received, and the characteristic of the channel is an extent that excessive noise was present or absent in the channel over time. In such embodiments, the value, which is indicative of the extent that excessive noise was present or absent in the channel over time, is adjusted based on results of the determining whether the received message was received in the presence or absence of excessive noise. In some such embodiments, a received message is processed if the received message was received in the absence of excessive noise and the IMD is maintained or switched to the normal state, and the received message is not processed if the IMD is maintained or switched to the noise state. In accordance with specific embodiments, the value is a noise value indicative of the presence of excessive noise when messages were received over time, and adjusting the noise value includes decreasing the noise value if the received message was received in the absence of excessive noise, or increasing the noise value if the received message was received in the presence of excessive noise. In accordance with other embodiments, the value is a quiescent value indicative of the absence of excessive noise when messages were received over time and/or indicative of the absence of excessive noise over time in the channel over which messages can be received, and adjusting the quiescent value includes increasing the quiescent value if a received message was received in the absence of excessive noise or if excessive noise was absent in the channel over which messages can be received, or decreasing the quiescent value if a received message was received in the presence of excessive noise or if excessive noise was present in the channel over which messages can be received.

Certain embodiments of the present technology are related to an implantable medical device (IMD) that is capable of switching between a normal state and a noise state. The IMD includes first and second receivers and at least one battery configured to power the first and second receivers and other components of the IMD. The first receiver is configured to selectively wakeup the second receiver. The second receiver when awake consuming more power than the first receiver. The IMD also includes at least one of a processor or controller configured to examine a received message and/or a channel over which messages can be received, and selectively adjust a value, indicative of a characteristic of messages received over time and/or a characteristic of the channel over time, based on results of a received message and/or the channel being examined. Such a value can be an invalidity value indicative of an extent of invalid messages received over time, a validity value indicative of an extent of valid messages received over time, a noise value indicative of a presence of excessive noise when messages were received over time, a noise value indicative of a presence of excessive noise over time in the channel, a quiescent value indicative of an absence of excessive noise when messages were received over time, or a quiescent value indicative of an absence of excessive noise over time in the channel, but is not limited thereto.

In accordance with certain embodiments of the present technology, the processor or controller of the IMD is also configured to compare the adjusted value to a first threshold if the IMD is in a normal state, or compare the value to a second threshold if the IMD is in a noise state. If the IMD is in the normal state, there is a determination whether to maintain the IMD in the normal state or switch the IMD to the noise state, based on results of the value being compared to the first threshold. If the IMD is in the noise state, there is a determination whether to maintain the IMD in the noise state or switch the IMD to the normal state, based on results of the value being compared to the second threshold. At least the second receiver of the IMD is put to sleep for a sleep period, if the IMD is maintained in or switched to the noise state. In accordance with specific embodiments, the IMD is a pacing device. When at least the second receiver is put to sleep, there may be no examining of any received messages. In accordance with certain embodiments, the IMD is configured to pace in accordance with a safe pacing mode when the second receiver is put to sleep, and the IMD is configured to pace in response to messages received from another IMD when the second receiver is not put to sleep. The IMD can be a leadless pacemaker (LP), but is not limited thereto.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

In some embodiments of an illustrative cardiac pacing system, pacing and sensing operations of multiple medical devices, which may include one or more leadless cardiac pacemakers, an implantable cardioverter-defibrillator (ICD), such as a subcutaneous-ICD, and/or a programmer reliably and safely coordinate pacing and/or sensing operations.

Figure 1:
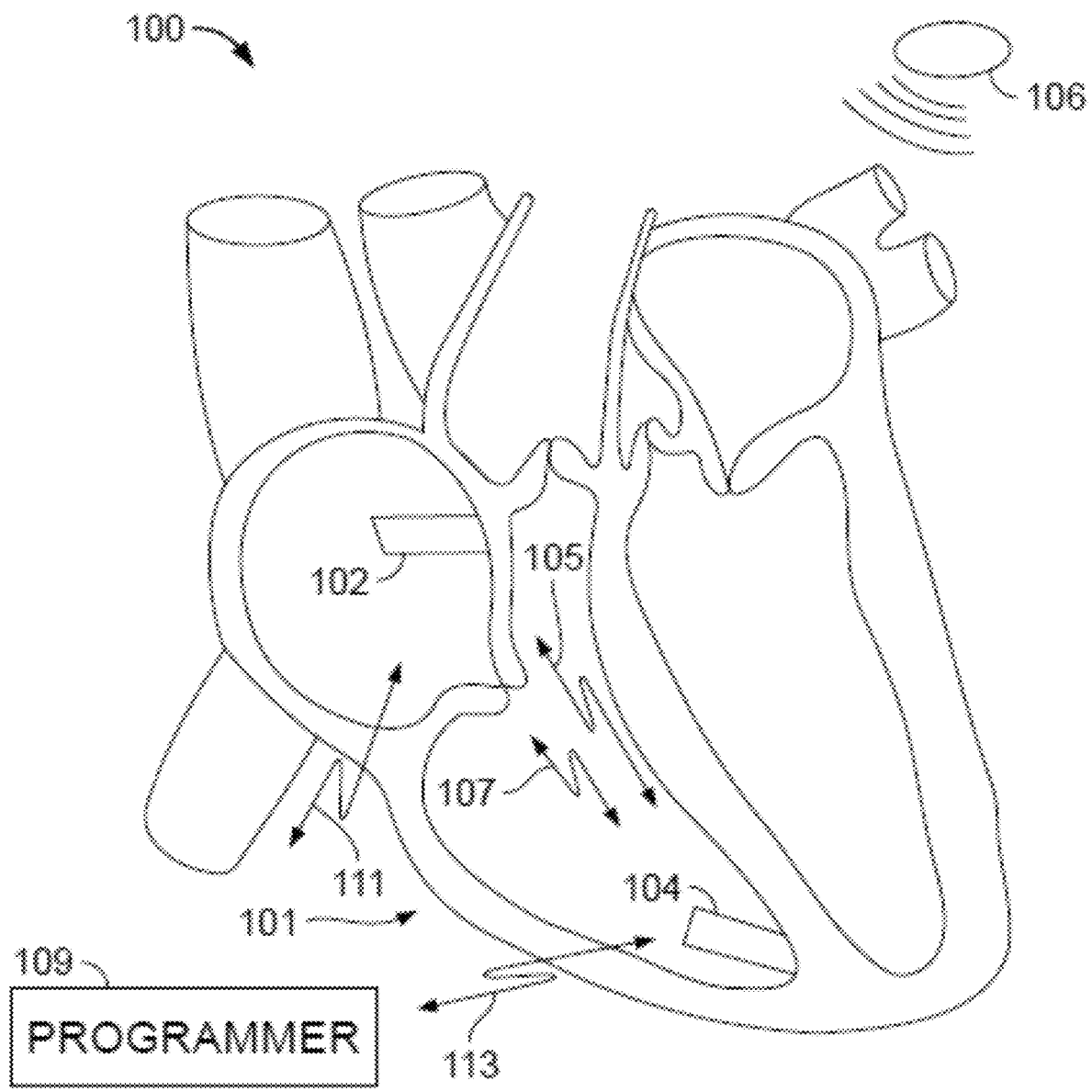
FIG. 1 illustrates a system formed in accordance with certain embodiments herein as implanted in a heart.

FIG. 1 illustrates a system 100 formed in accordance with certain embodiments herein as implanted in a heart 101. The system 100 comprises two or more leadless pacemakers (LPs) 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more leadless cardiac pacemakers 102 and 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the programmer 109, and the ICD 106.

In accordance with certain embodiments, methods are provided for coordinating operation between leadless pacemakers (LPs) located in different chambers of the heart. The methods configure a local LP to receive communications from a remote LP through conductive communication.

While the methods and systems described herein include examples primarily in the context of LPs, it is understood that the methods and systems herein may be utilized with various other external and implanted devices. By way of example, the methods and systems may coordinate operation between various implantable medical devices (IMDs) implanted in a human, not just LPs. The methods and systems comprise configuring a first IMD to receive communications from at least a second IMD through conductive communication over at least a first channel. It should also be understood that the methods and systems may coordinate operation between multiple IMDs, and are not limited to coordinate operation between just a first and second IMD. The methods and systems may also be used to coordinate operation of two or more IMDs implanted within the same chamber that may be the same type of IMD or may be different types of IMDs. The methods and systems may also be used to coordinate operation of two or more IMDs in a system comprising at least one IMD implanted but not within a heart chamber, e.g., epicardially, transmurally, intravascularly (e.g., coronary sinus), subcutaneously (e.g., S-ICD), etc.

Figure 2:
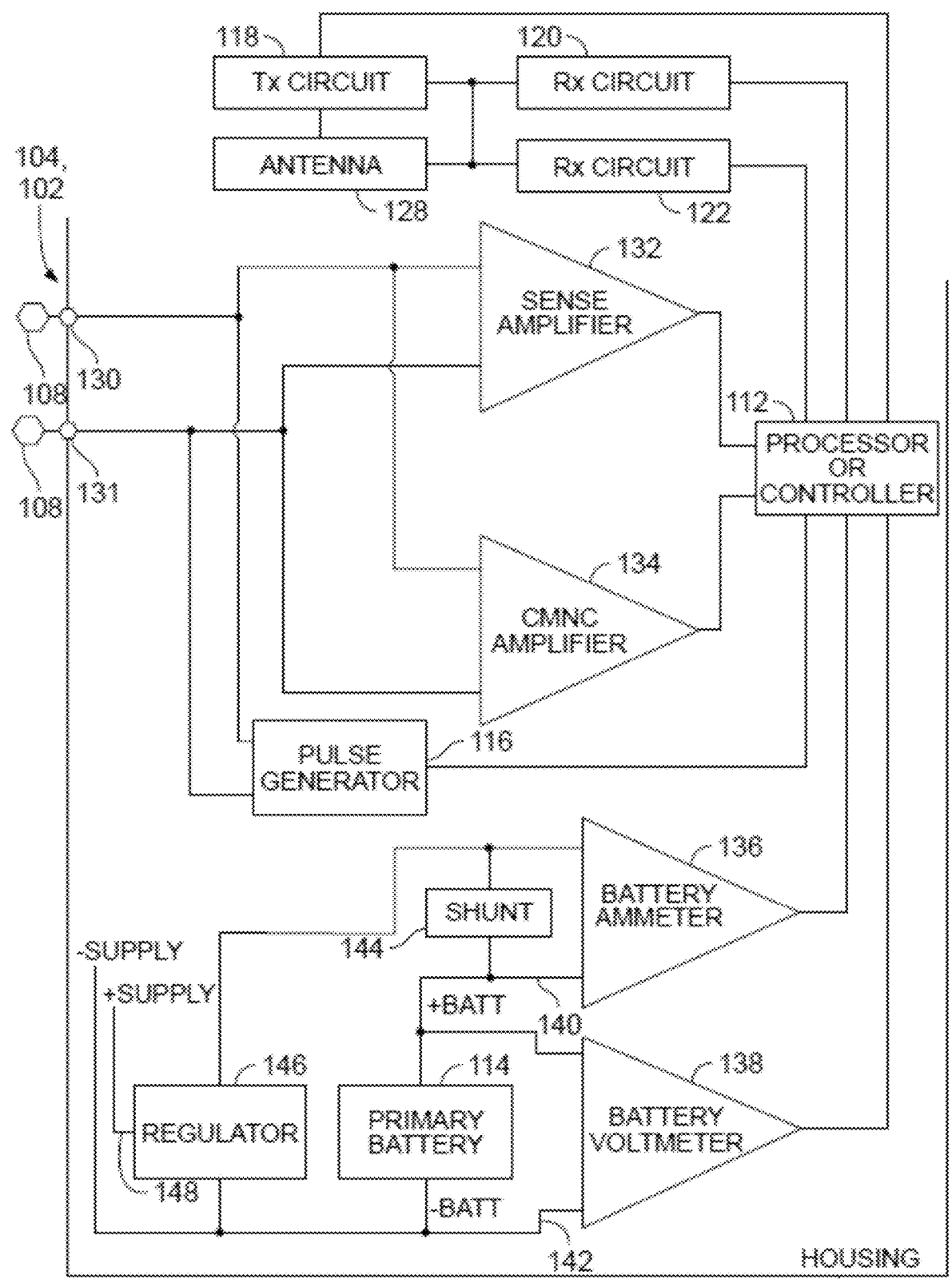
FIG. 2 is a block diagram of a single LP in accordance with certain embodiments herein.

Referring to FIG. 2, a pictorial diagram shows an embodiment for portions of the electronics within LP 102, 104 configured to provide conducted communication through the sensing/pacing electrode. One or more of LPs 102 and 104 comprise at least two leadless electrodes 108 configured for delivering cardiac pacing pulses, sensing evoked and/or natural cardiac electrical signals, and uni-directional or bidirectional communication.

LP 102, 104 includes a transmitter 118 and first and second receivers 120 and 122 that collectively define separate first and second communication channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. LP 102, 104 may also include one or more transmitters in addition to transmitter 118. In certain embodiments, LPs 102 and 104 may communicate over more than just first and second communication channels 105 and 107. In certain embodiments, LPs 102 and 104 may communicate over one common communication channel 105. The transmitter 118 and receiver(s) 120, 122 may each utilize a separate antenna or may utilize a common antenna 128. Optionally, LPs 102 and 104 communicate conductively over a common physical channel via the same electrodes 108 that are also used to deliver pacing pulses. Usage of the electrodes 108 for communication enables the one or more leadless cardiac pacemakers 102 and 104 for antenna-less and telemetry coil-less communication.

When LP 102, 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice or wakeup pulse) followed by an event marker. The notice trigger pulse is transmitted over a first channel (e.g., with a pulse duration of approximately 10 μs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant to implant (i2i) communication from another LP (or other IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Some embodiments described herein provide efficient and reliable processes to maintain synchronization between LPs 102 and 104 without maintaining continuous communication between LPs 102 and 104. In accordance with certain embodiments herein, the transmitter(s) 118 and receiver(s) 120, 122 utilize low power event messages/signaling between multiple LPs 102 and 104. The low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communications in time slots having duration of 10-20 µs, where the Tx/Rx time slots occur periodically (e.g., every 10-20 ms). In the foregoing example, a receiver 120, 122 that is active/ON (also referred to as awake) for select receive time slots, that are spaced apart several milliseconds, may draw an amount of current that is several times less (e.g., 1000× less) than a current draw of a receiver that is "always on" (always awake).

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of ⅕₀₀ to ¹⁄₁₀₀₀₀. A gain factor may be ¹⁄₁₀₀₀th. Transmit current is a design factor in addition to receiver current. As an example, the system may allocate one-half of the implant communication current budget to the transmitter (e.g., 0.5 µA for each transmitter). When LP 102, 104 maintains a transmitter in a continuous on-state and the electrode load is 500 ohms, a transmitted voltage may be 0.250 mV. When an event signal is transmitted at 0.250 mV, the event signal is attenuated as it propagates and would appear at LP 102, 104 receiver as an amplitude of approximately 0.25 µV. The receivers 120 and 122 utilize a synchronization threshold to differentiate incoming communication signals from noise. As an example, the synchronization threshold may be 0.5 µV (or more generally 0.25 µV to 5 µV), which would cause LP 102, 104 receiver to reject an incoming communication signal that exhibits a receive voltage below 0.5 µV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

When LP transmitter 118 transmits event signals over a conductive communication channel that has an electrode load of 500 ohm using a 1 ms pulse width at 2.5V at a rate of 60 bpm, LP transmitter 118 will draw 4.4 µA for transmit current. When LP transmitter 118 transmits event signals at 2.5V using a 2 µs pulse width, transmitter 118 only draws 10 nA to transmit event messages at a rate of 60 bpm. In order to sense an event message (transmitted with the foregoing parameters), receivers 120 and 122 may utilize 50 µA. In accordance with certain embodiments herein, the pulse widths and other transmit/receive parameters may be adjusted to achieve a desired total (summed) current demand from both transmitter 118 and receivers 120 and 122. The transmitter current decreases nearly linearly with narrowing bandwidth (pulse width), while a relation between receiver current and bandwidth is non-linear.

In accordance with certain embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel. First receiver 120 may maintain the first channel active (awake) for at least a portion of a time when the second channel is inactive (asleep) to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP).

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102, 104 may implement a handshaking protocol in which the Tx and Rx LP 102, 104 exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, with LP 102, 104 utilizing the same communication scheme. The external programmer may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse width. The foregoing pacing parameters correspond to a current draw of about 1.9 µA. The same LP 102, 104 may implement an event message utilizing event signaling parameters for amplitude, pulse width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102, 104 senses an intrinsic event, the transmitter sends a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102, 104 may use larger pulse widths.

By combining event messages and low power pacing, LP 102, 104 may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

For example, when an LP 102, 104 does not receive an event message within a select time out interval, LP 102, 104 may resend an event message at a higher amplitude. As another example, LP 102, 104 may perform an event signaling auto-level search wherein the LPs send event messages at progressively higher amplitude until receiving confirmation that an event message was received (or receiving a subsequent event message from another LP). For example, in DDD mode when the atrial or ventricular LP 102, 104 does not see an event signal from LP 102, 104 in the other chamber before its timeout interval it could automatically raise the amplitude of the event message, until the LPs 102 and 104 become and remain in sync. Optionally, LP 102, 104 may implement a search hysteresis algorithm similar to those used for rate and amplitude capture to allow the lowest safe detectible amplitude to be determined.

The LPs 102 and 104 may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102, 104 configured for implantation in electrical contact with a cardiac chamber and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
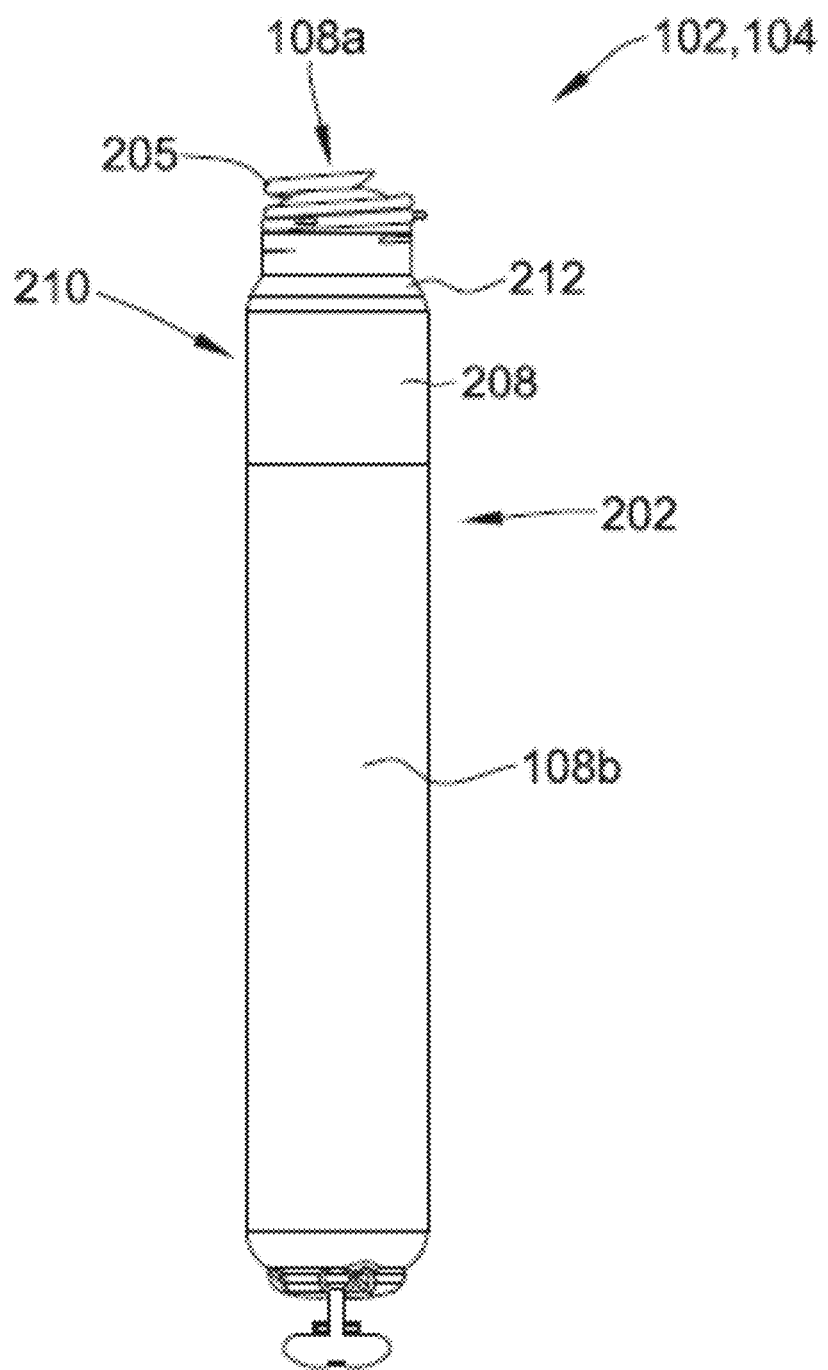
FIG. 3 illustrates a LP in accordance with certain embodiments herein.

FIG. 3 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-To-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
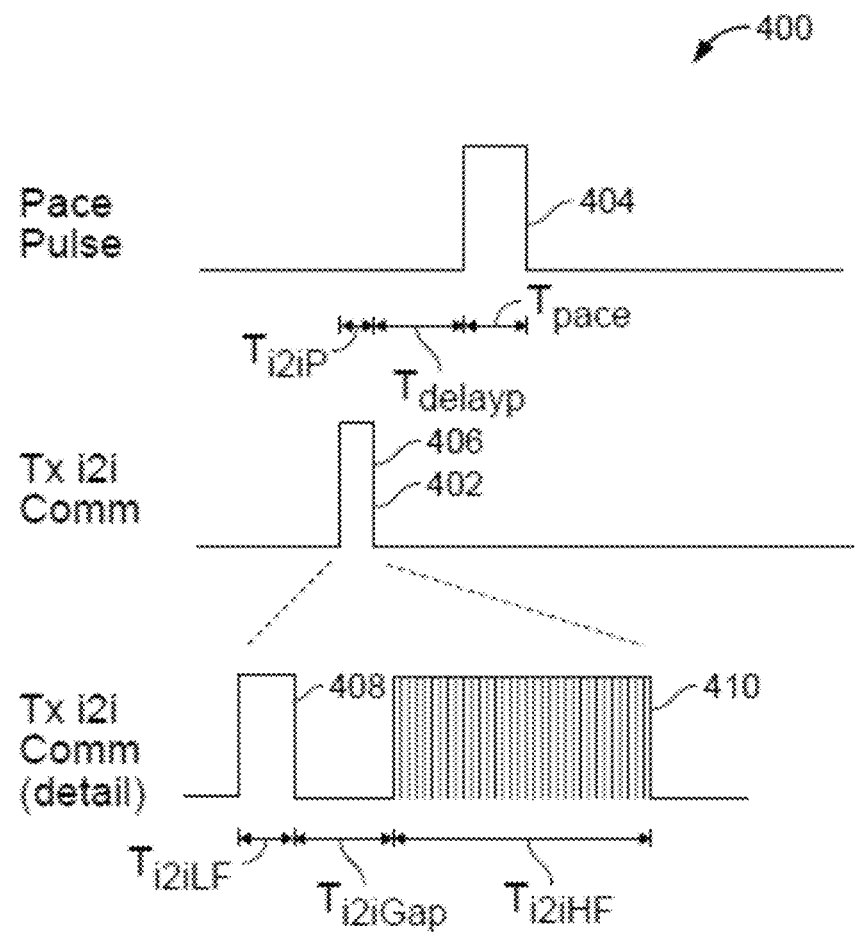
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102 to LP 104. As shown in FIG. 4, in this embodiment, an i2i transmission 402 is sent prior to delivery of a pace pulse 404 by the transmitting LP (e.g., LP 102). This enables the receiving LP (e.g., LP 104) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 5:
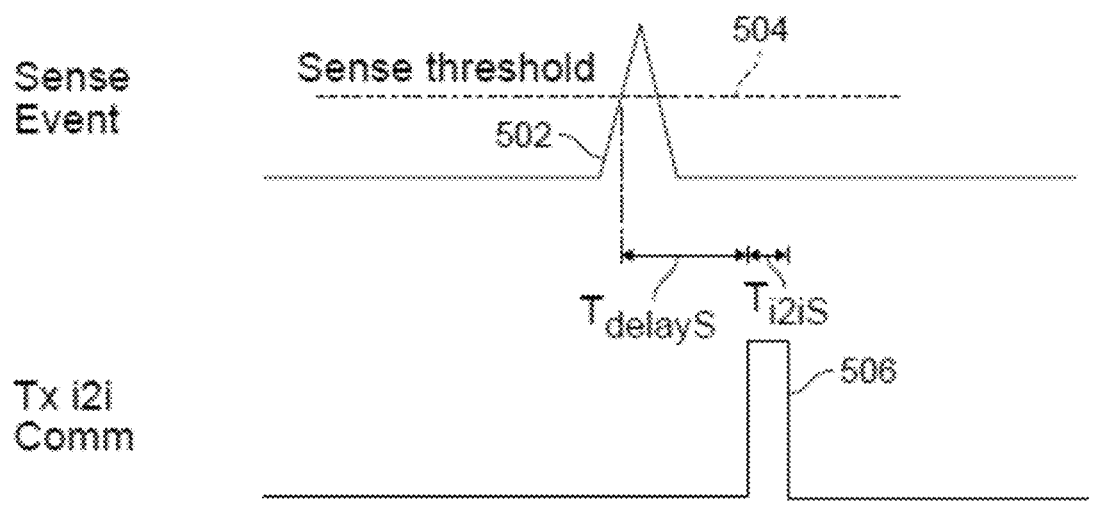
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102 to LP 104. As shown in FIG. 5, in this embodiment, the transmitting LP (e.g., LP 102) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

| "A2V" Markers/Commands (i.e., from aLP to vLP) | | |
|---|---|---|
| Marker | Description | Result in vLP |
| AS | Notification of a sensed event in atrium (if not in PVAB or PVARP) | Initiate AV interval (if not in PVAB or PVARP) |
| AP | Notification of a paced event in atrium | Initiate PAVB<br>Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

| "V2A" Markers/Commands (i.e., from vLP to aLP) | | |
|---|---|---|
| Marker | Description | Result in aLP |
| VS | Notification of a sensed event in ventricle | Initiate PVARP |
| VP | Notification of a paced event in ventricle | Initiate PVAB<br>Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

Mitigating Excessive Wakeups in Dual Chamber Leadless Pacemaker

As explained above, each of LPs 102 and 104 may include first and second receivers 120 and 122 that operate with different first and second activation protocols and different first and second receive channels. As also explained above, the first and second receivers 120 and 122 of each of the LPs 102 and 104 can enable the LPs 102 and 104 to implement a staged receiver wakeup scheme in order to improve reliability yet remain power efficient. For example, the first receiver 120 may be assigned a first activation protocol that by default causes the first receiver 120 to be normally "on" or "awake" or "active" (which terms are used interchangeably herein) and listening for messages received over a first receive channel that has a lower fundamental frequency range/pulse duration (e.g., 1 kHz to 100 kHz/10 μs to approximately 1 ms) as compared to a fundamental frequency range (e.g., greater than 100 kHz/less than 10 μs per pulse) assigned to the second receive channel. The first receiver 120 may maintain the first channel active for at least a portion of a time when the second channel is inactive, so that the first receiver 120 can listen for event messages from a remote LP. The controller or processor of the LP can determine whether the incoming signal received over the first channel corresponds to an LP wakeup notice. The second receiver 122 may be assigned a second activation protocol that is a triggered protocol, in which the second receiver 122 is normally "off" or "asleep" or "inactive" (which terms are used interchangeably herein) and becomes active in response to detection of trigger events over the first receive channel (e.g., when the incoming signal corresponds to the LP wakeup notice, activating the second channel at the local LP). In other words, in order to conserve power the second receiver 122 can be asleep unless awaken by the first receiver 120. Depending upon implementation, when the second receiver 122 is asleep, it can either be in a low power mode or completely disconnected from a power supply. Regardless of the implementation, the second receiver 122 will consume less power when it is asleep compared to when it is awake. Similarly, the first receiver 120 will consume less power when it is asleep compared to when it is awake. When both the first and second receivers are awake the second receiver consumes more power than the first receiver.

The first receiver 120 of a given LP (e.g., 102) can also be referred to as a low power low bandwidth receiver, since it is configured to operate at a lower power and a lower bandwidth than the second receiver 122 does when the second receiver 122 is awake. Conversely, the second receiver 122 of the LP (e.g., 102) can also be referred to as a high power high bandwidth receiver, since it is configured to operate at a higher power and a higher bandwidth than the first receiver 120 does when the second receiver 122 is awake. In accordance with certain embodiments of the present technology, in order to conserve power, as part of i2i communication, a signal received by the low power low bandwidth receiver (i.e., the first receiver 120) is used to wakeup the high power high bandwidth receiver (i.e., the second receiver 122), using what can be referred to as a two-step wakeup process. In the two-step wakeup process, the first receiver 120 of a device (e.g., the LP 102) can be normally awake and listening for messages while the second receiver 122 is normally asleep and only woken up by the first receiver 120 when the first receiver 120 receives a portion of a message (e.g., the low frequency pulse 408) that also includes another portion (e.g., the high frequency pulse train 416) that is to be received and decoded using the second receiver 122.

A potential problem with the aforementioned two-step wakeup process is that the low power low bandwidth receiver (i.e., the first receiver 120) may be very sensitive to electrical noise. More specifically, in an electrically noisy environment, the high sensitivity of the first receiver 120 to electrical noise may cause the first receiver 120 to frequently trigger wakeups of the second receiver 122 when unnecessary. This can lead to significant power consumption and a shorter battery life of the LP, and thus, a reduction in the useful life of the LP (e.g., 102). A triggered wakeup of the second receiver 122 is considered unnecessary, for example, where the wakeup was triggered in response to noise that was mistaken for a valid message, as opposed to being triggered in response to an actual valid message being received from another LP (e.g., 104). Exemplary types of valid messages that an LP (e.g., 102) can receive from another LP (e.g., 104) include, but are not limited to, the event messages that were described above with reference to FIGS. 1-5 and Tables 1 and 2.

Certain embodiments of the present technology mitigate and preferably prevent the first receiver 120 from unnecessarily waking up the second receiver 122 of a device, such as an LP (e.g., 102). In certain embodiments, if the first receiver 120 triggers the wakeup of the second receiver 122, but the triggered wakeup is not followed (within a specified amount of time) by the second receiver 122 receiving and decoding a valid message, then the wakeup is considered invalid, or more generally, the received message that caused the first receiver 120 to wakeup the second receiver 122 can be considered an invalid message. In accordance with an embodiment, the device (e.g., the LP 102) calculates the average number of invalid wakeups over time, or more generally, the device calculates a value indicative of an extent of invalid messages received over time. If this value exceeds a specified threshold, the device enters a Noise State. In the Noise State, the device can operate in a safe pacing mode (e.g., VVI or VOO) that does not depend on i2i communication. In the Noise State, the device periodically checks to see if valid messages are arriving. If the device receives valid messages for at least a specified amount of time, the device leaves the Noise State and returns to a Normal State where normal i2i communication resumes. In accordance with certain embodiments, the first and second receivers 120 and 122 are enabled only periodically when the device is in an electrically noise environment, and more specifically in the Noise State, thereby conserving power and thus improving battery and device longevity. An implementation of an embodiment to mitigate and preferably prevent a first receiver (e.g., 120) from unnecessarily waking up a second receiver (e.g., 122) of a device, such as an LP (e.g., 102), is described below with reference to the high level flow diagram of FIG. 6. The methods described with reference to FIG. 6, and with reference to FIGS. 7 through 10, can be performed under the control of a processor or controller (e.g., 112 in FIG. 2, or 1120 in FIG. 11). In other words, a processor or controller can be configured to perform various aspects of the present technology.

Figure 6:
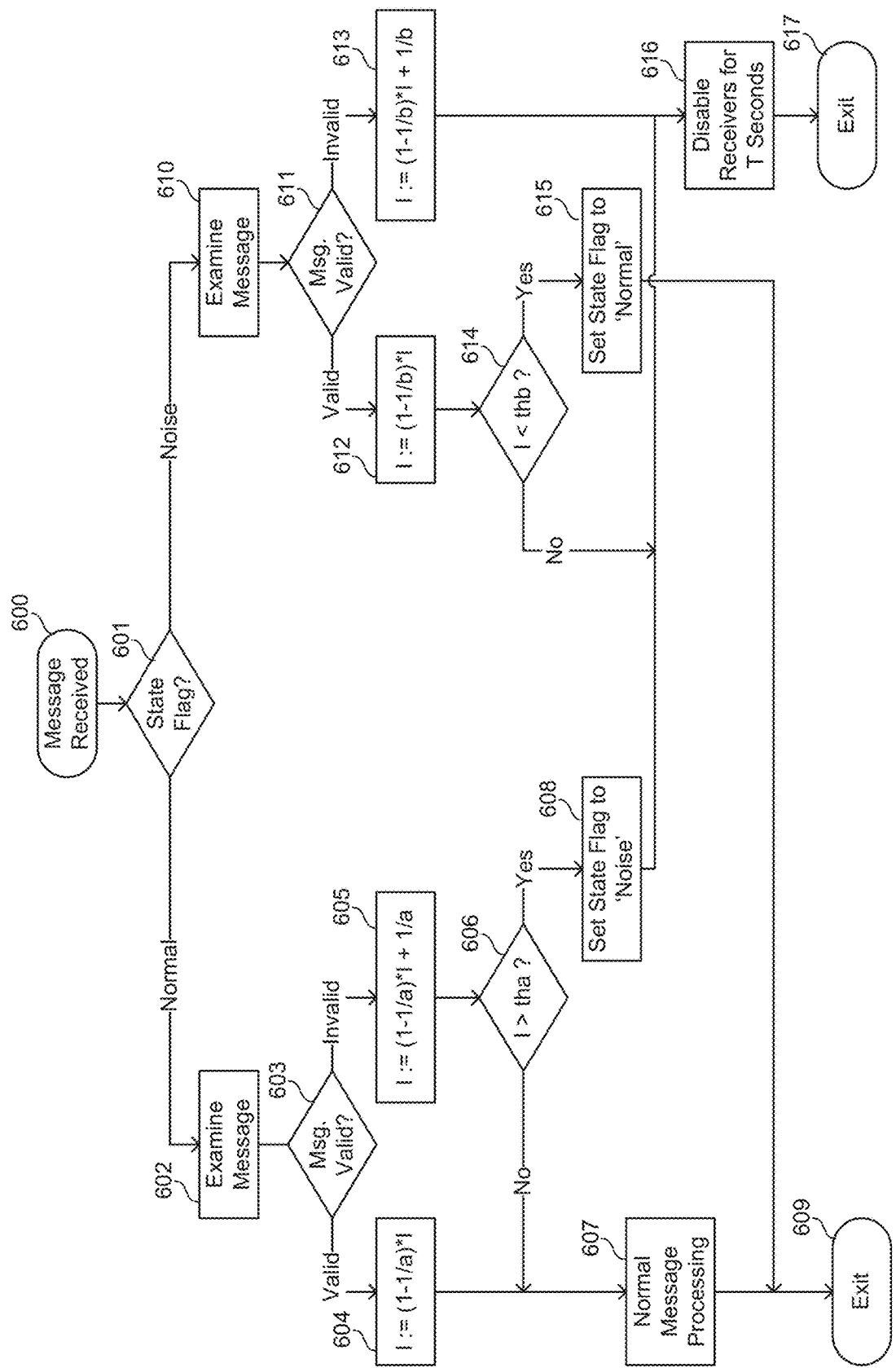
FIGS. 6, 7, 8 and 9 are high level flow diagrams that are used to summarize methods according to various embodiments of the present technology that reduce how often a first receiver of a device wakes up a second receiver of the device and thereby reduces power consumed by the device.

Referring to FIG. 6, Block 600, "Message Receive" is the entry point for the method. This means that hardware of a device, which will be assumed to be the LP 102 for this description, has received a low-bandwidth signal (e.g., the low frequency pulse 408 described above with reference to FIG. 4) via the first receiver 120 (i.e., the low-power low-bandwidth receiver), and has triggered the waking up of the second receiver 122 (i.e., the high-power high-bandwidth receiver), and has attempted to receive an i2i message. The i2i message, which can be referred to more succinctly as a message, may be valid or invalid. In other words, at Block 100, the first receiver 120 receives a message, which may be a valid message or an invalid message.

The term "message", as used herein, can refer to an actual sent message that is received and is capable of being decoded by the second receiver 122, an actual sent message that is received but is too noisy to be decoded by the second receiver 122, an actual sent message that is received but due to noise it is decoded mistakenly for a different message, noise that is initially mistaken for being an actual message but is sufficiently different than an actual message so that it cannot be decoded by the second receiver 122, as well as noise that is received and is mistaken for being an actual message and is decoded by the IMD because the noise is sufficiently similar to an actual message. The term "valid message", as used herein, can refer to an actual sent message that is received and is capable of being decoded by the second receiver 122, an actual sent message that is received but due to noise it is decoded mistakenly for a different message (this may occur in rare circumstances), or noise that is received and is mistaken for being an actual message and is decoded by the IMD because the noise is sufficiently similar to an actual message (this may occur in very rare circumstances). The latter two types of a "valid message", which may occur in rare or very rare circumstances, are examples false positives. Accordingly, it is possible that a "valid message" is not an actual message, or is an actual message that has been decoded incorrectly. The term "invalid message", as used herein, can refer to an actual sent message that is received but is too noisy to be decoded by the second receiver 122, as well as noise that is initially mistaken for being an actual message but is sufficiently different than an actual message so that it cannot be decoded by the second receiver 122. In accordance with certain embodiments, the determination of whether a message is valid or invalid can be performed by a processor or controller that performs error detection or correction.

Block 601 is a decision block based on a State Flag that indicates whether the LP 102 is currently in a Normal state or a Noise state. The State Flag can be a binary value, saved in a memory location or in a register, which indicates whether the LP 102 is currently in its Normal State or its Noise State. A Normal path, shown at the left in FIG. 6, is processing that occurs when the i2i communication appears to be normal, or more generally, occurs when the LP 102 is in its Normal State. The Noise path, shown at the right in FIG. 6, is the processing that occurs in a noisy environment, or more generally, when the LP 102 is in its Noise State. The Normal path will initially be discussed, which path is followed when the LP 102 is in its Normal State.

Block 602, "Examine Message" is the processing to examine the received message bits and to determine whether the message is valid or invalid. The message that is examined at block 602 can be an actual sent message, or can be noise that is initially mistakenly interpreted as being an actual sent message. In accordance with certain embodiments, the validity depends on whether a time-out occurred before the second receiver 122 was able to decode the message, wherein such decoding can involve identifying consistency with respect to redundant information in the message format (e.g. duplicate bits, CRC, etc.). More generally, at Block 602 the received message is examined to determine whether the message is valid or invalid.

Block 603, is a decision block that depends on the whether the message was valid or invalid for the Normal State.

If the message was valid, Block 604 is performed. This block effectively decreases the variable "I" which essentially represents a time average of the number of invalid messages. In other words, a value of the variable "I" is indicative of the extent of invalid messages received over time. In an embodiment, the variable "I" ranges from 0 to 1 and is calculated by a single-pole digital low pass filter algorithm $I:=(1-1/a)*I$. As a result, the low pass filter algorithm implements an exponentially weighted average. The time constant parameter "a" controls the rate of change or equivalently the weighting. Other ways of decreasing the variable I are also possible and within embodiments of the present technology.

Block 605 is performed if the message was determined to be invalid. This block increases the value of the variable "I", which as noted above essentially represents a time average of the number of invalid messages, and more generally is indicative of the extent of invalid messages received over time. In an embodiment, the single-pole low pass filter algorithm $I:=(1-1/a)*I+1/a$ is used to increase the value of "I" at Block 605. Other ways of increasing the variable I are also possible and within embodiments of the present technology.

Block 606 checks to see if I exceeds a first threshold parameter "tha". Exceeding the first threshold parameter tha is an indication that the device is in an electrically noisy environment. In accordance with an embodiment, the first threshold parameter tha is in the range of 0 to 1. For example, tha can be 0.6.

Block 608, which is performed if the first threshold parameter tha is exceeded, sets the device into the Noise State. This can involve changing a State Flag from 0 to 1, or vice versa, depending upon implementation.

Block 607 is normal message processing. Following normal processing, the method exits in Block 609. Normal processing of a received valid message can involve the device being responsive to the valid message, e.g., by performing pacing in response to the valid message.

The Noise path, shown at the right in FIG. 6 will now be discussed, which path is followed when the LP 102 is in its Noise State. If the device is in the Noise State, Block 610 is performed, which does the same function as Block 602. Block 611 checks the validity of the messages similar to Block 603.

If the message was valid, Block 612 decreases the variable "I", which as noted above is indicative of the extent of invalid messages received over time. Again a low pass filter algorithm can be used to implement an exponentially weighted average. More specifically, a single-pole digital low pass filter algorithm $I:=(1-1/b)*I$ can be used at Block 612. Here, the time constant parameter "b" controls the rate and, in accordance with an embodiment, is different from the parameter "a" because it can be desirable to have a different timing to resume normal operation and because the update rate for this path will be less frequent. It is also possible that the parameter "b" is the same as the parameter "a".

Decision Block 614 decides whether the variable I has fallen sufficiently to warrant return to the Normal State. This is performed by checking to see if the variable I is less than a second threshold parameter "thb". In accordance with an embodiment, the second threshold parameter thb is in the range of 0 to 1 and is less than the first threshold parameter tha in order to provide hysteresis. For example, thb can be 0.3. It is also possible that the second threshold parameter thb is the same as the first threshold parameter tha, but this is less preferred as it may result in constant toggling back between the Normal State and the Noise State without any hysteresis.

Block 615 performs the state change to the Normal State.

Block 613 is performed when the device is in the Noise State and the received message is invalid. This block causes the variable I to increase, indicating that the average number of invalid messages is greater, and more generally indicates an increase in the extent of invalid messages received over time. In an embodiment, the single-pole low pass filter algorithm $I:=(1-1/b)*I+1/b$ is used to increase the value of "I" at Block 613. Other ways of updating the variable I are also possible and within embodiments of the present technology.

Block 616, "Disable Receiver(s) for T seconds" is performed in the Noise State and conserves power by ensuring that the power consuming high-bandwidth receiver is put to sleep. The i2i messages will be resampled after this time T expires. At Block 616, both the first and second receivers 120 and 122 can be put to sleep for T seconds, or just the second receiver 122 can be put to sleep for T seconds. More generally, at Block 616 at least one of the first and second receivers is put to sleep for at least a sleep period of T seconds. The method exits through Block 617. In an electrically noisy environment, this method turns on (or more generally, awakens) the receivers every T seconds rather than continually, thus conserving battery energy. T can be within the range of 5 seconds to 600 second, e.g., 60 seconds, but is not limited thereto. In accordance with certain embodiments, T is a programmed value that is specified, e.g., by a manufacturer, clinician or physician. In accordance with other embodiments, it is possible to extend T up to a limit if received messages continue to be invalid, which would afford greater power conservation at the expense of taking longer to return to normal operation. In other words, T may be selectively increased or decreased based on the results of examining a received message. The time period specified by the value T can be referred to as the sleep period.

In the embodiments described above with reference to FIG. 6, a variable "I" that is indicative in the extent of invalid messages received over time is adjusted and used to determine when the device should be in a Normal State or a Noise State. The variable "I" can also be referred to as an invalidity value indicative of the extent of invalid messages received over time.

In alternative embodiments, described below with reference to FIG. 7, a variable "V" that is indicative of the extent of valid messages received over time is adjusted and used to determine when the device should be in a Normal State or a Noise State. The variable "V" can also be referred to as a validity value indicative of the extent of valid messages received over time.

Figure 7:
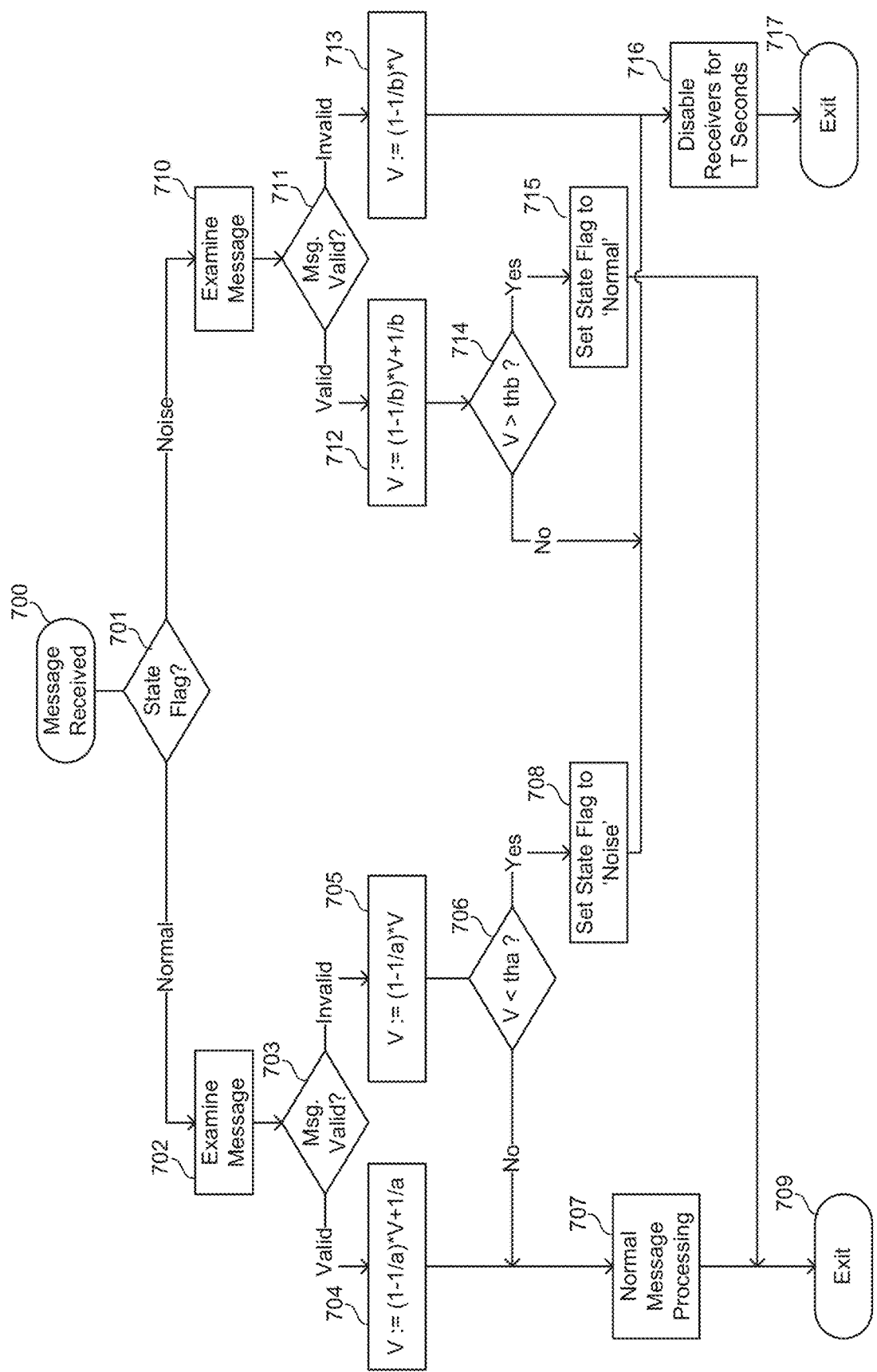

Referring to FIG. 7, Blocks 700, 702, 703, 710 and 711 are the same, respectively, as Blocks 600, 602, 603, 610 and 611 described above with reference to FIG. 6, and thus, need not be described in detail again.

Block 703, is a decision block that depends on the whether the message was valid or invalid for the Normal State, as was Block 603.

If the message was valid, Block 704 is performed. This block effectively increases the variable "V" which essentially represents a time average of the number of valid messages. In other words, a value of the variable "V" is indicative of the extent of valid messages received over time, as noted above. In an embodiment, the variable "V" ranges from 0 to 1 and is calculated by a single-pole digital low pass filter algorithm $V:=(1-1/a)*V+1/a$. As a result, the low pass filter algorithm implements an exponentially weighted average. The time constant parameter "a" controls the rate of change or equivalently the weighting, as was the case in the embodiment of FIG. 6. Other ways of increasing the variable I are also possible and within embodiments of the present technology.

Block 705 is performed if the message was determined to be invalid. This block decreases the value of the variable "V", which as noted above essentially represents a time average of the number of valid messages, and more generally is indicative of the extent of valid messages received over time. In an embodiment, the single-pole low pass filter algorithm $V:=(1-1/a)*V$ is used to decrease the value of "V" at Block 705. Other ways of decreasing the variable V are also possible and within embodiments of the present technology.

Block 706 checks to see if V is less than a first threshold parameter "tha". Being less than the first threshold parameter tha is an indication that the device is in an electrically noisy environment. In accordance with an embodiment, the first threshold parameter tha is in the range of 0 to 1. For example, tha can be 0.6.

Block 708, which is performed if V is less than the first threshold parameter tha, sets the device into the Noise State. This can involve changing a State Flag from 0 to 1, or vice versa, depending upon implementation.

Block 707 is normal message processing. Following normal processing, the method exits in Block 709. Normal processing of a received valid message can involve the device being responsive to the valid message, e.g., by performing pacing in response to the valid message.

The Noise path, shown at the right in FIG. 7 will now be discussed, which path is followed when the LP 102 is in its Noise State. If the device is in the Noise State, Block 710 is performed, which does the same function as Block 702. Block 711 checks the validity of the messages similar to Block 703.

If the message was valid, Block 712 increases the variable "V", which as noted above is indicative of the extent of valid messages received over time. Again a low pass filter algorithm can be used to implement an exponentially weighted average. More specifically, a single-pole digital low pass filter algorithm $V:=(1-1/b)*V+1/b$ can be used at Block 712. Here, the time constant parameter "b" controls the rate and, in accordance with an embodiment, is different from the parameter "a" because it can be desirable to have a different timing to resume normal operation and because the update rate for this path will be less frequent, as was also the case in the embodiment of FIG. 6. It is also possible that the parameter "b" is the same as the parameter "a". Decision Block 714 decides whether the variable V has increased sufficiently to warrant return to the Normal State. This is performed by checking to see if the variable V is greater than a second threshold parameter "thb". In accordance with an embodiment, the second threshold parameter thb is in the range of 0 to 1 and is greater than the first threshold parameter tha in order to provide hysteresis. It is also possible that the second threshold parameter thb is the same as the first threshold parameter tha, but this is less preferred as it may result in constant toggling back between the Normal State and the Noise State without any hysteresis.

Block 715 performs the state change to the Normal State.

Block 713 is performed when the device is in the Noise State and the received message is invalid. This block causes the variable V to decrease, indicating that the average number of valid messages is reduced, and more generally indicatives a decrease in the extent of valid messages received over time. In an embodiment, the single-pole low pass filter algorithm $V:=(1-1/b)*V$ is used to decrease the value of "V" at Block 713. Other ways of updating the variable V are also possible and within embodiments of the present technology.

Block 716 is the same as Block 616, and thus its details need not be repeated.

In alternative embodiments, described below with reference to FIG. 8, a variable "N" that is indicative of the extent that excessive noise was present when messages were received over time is adjusted and used to determine when the device should be in a Normal State or a Noise State. The variable "N" can also be referred to as a noise value indicative of the extent of excessive noise received over time.

Figure 8:
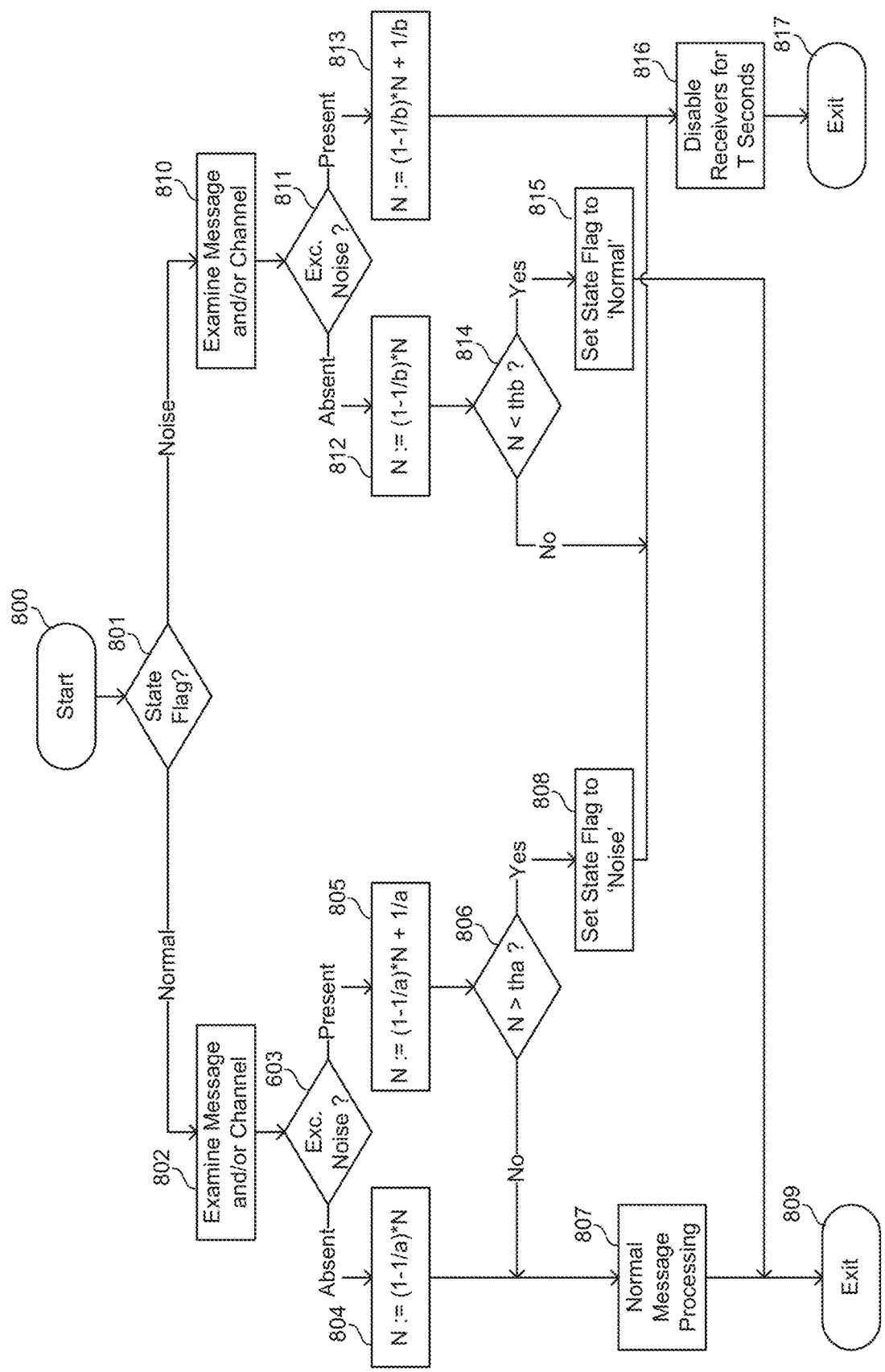

Referring to FIG. 8, Block 800 is the entry point for the method. This method can be triggered by a message being received, which can mean that hardware of a device, which will be assumed to be the LP 102 for this description, has received what appears to be a low-bandwidth signal (e.g., the low frequency pulse 408 described above with reference to FIG. 4) via the first receiver 120 (i.e., the low-power low-bandwidth receiver), and has triggered the waking up of the second receiver 122 (i.e., the high-power high-bandwidth receiver), and has attempted to receive an i2i message. The i2i message, which can be referred to more succinctly as a message, may be receive in the presence or absence of excessive noise. In other words, at Block 800, the first receiver 120 may have received a message, which may be received when excessive noise is present or absent. The method described with reference to FIG. 8 can alternatively be performed periodically, or in response to a triggering event other than receiving a message.

As noted above in the discussion of FIG. 6, the term "message", as used herein, can refer to an actual sent message that is received and is capable of being decoded by the second receiver 122, an actual sent message that is received but is too noisy to be decoded by the second receiver 122, an actual sent message that is received but due to noise it is decoded mistakenly for a different message, noise that is initially mistaken for being an actual message but is sufficiently different than an actual message so that it cannot be decoded by the second receiver 122, as well as noise that is received and is mistaken for being an actual message and is decoded by the IMD because the noise is sufficiently similar to an actual message. When a message is received in the absence of excessive noise, this means an actual message is received and is capable of being decoded by the second receiver 122. When a message is received in the presence of excessive noise, this can mean that an actual message is received but is too noisy to be decoded by the second receiver 122, as well as can mean that noise that is initially mistaken for being an actual message cannot be decoded by the second receiver 122 because there is actually no message.

Block 801 is a decision block based on a State Flag that indicates whether the LP 102 is currently in a Normal state or a Noise State. The State Flag can be a binary value, saved in a memory location or in a register, which indicates whether the LP 102 is currently in its Normal State or its Noise State. A Normal path, shown at the left in FIG. 8, is processing that occurs when the i2i communication appears to be normal, or more generally, occurs when the LP 102 is in its Normal State. The Noise path, shown at the right in FIG. 8, is the processing that occurs in a noisy environment, or more generally, when the LP 102 is in its Noise State. The Normal path will initially be discussed, which path is followed when the LP 102 is in its Normal State.

Block 802, "Examine Message and/or Channel" is the processing to examine the received message bits and to determine whether the message (which as noted above, can actually be noise initially mistakenly interpreted to be an actual message) was received in the presence or absence of excessive noise, and/or is the processing to determine whether there was the presence or absence of excessive noise in the channel over which messages can be received. In accordance with certain embodiments, a determination can depend on whether a time-out occurred before the second receiver 122 was able to decode a received message, wherein such decoding can involve identifying consistency with respect to redundant information in the message format (e.g. duplicate bits, CRC, etc.). In accordance with other embodiments, determining whether a message was received in the presence or absence of excessive noise can involve determining whether one or more characteristics, e.g., pulse width, pulse amplitude and/or pulse interval, of the received message is/are within expected ranges, and/or the like. For example, referring back to FIG. 4, the characteristics that can be examined at block 802 can be associated with the low frequency pulse 408 and/or the high frequency pulse train 410 of an envelope 406 of an i2i transmission 402 but are not limited thereto. Other variations are also possible, and within the scope of embodiments of the present technology. More generally, at Block 802 the received message can be examined to determine whether the message was received in the presence or absence of excessive noise. Instead of (or in addition to) examining a message at Block 802, a channel over which messages can be received may be examined to determine whether excessive noise is present in or absent from the channel.

Block 803, is a decision block that depends on the whether the message was received in the presence or absence of excessive noise for the Normal State, and/or whether the excessive noise was present in or absent from the channel over which message can be received.

If a message was received in the absence of excessive noise, or if there was an absence of excessive noise in the channel over which messages can be received, Block 804 is performed. This block effectively decreases the variable "N" which essentially represents a time average of the number of messages received in the presence of excessive noise or represents a time average of excessive noise being present in the channel. In other words, a value of the variable "N" is indicative of the extent that messages were received in the presence of excessive noise over time, and/or the extent that excessive noise over time was present in the channel. In an embodiment, the variable "N" ranges from 0 to 1 and is calculated by a single-pole digital low pass filter algorithm N:=(1−1/a)*N. As a result, the low pass filter algorithm implements an exponentially weighted average. The time constant parameter "a" controls the rate of change or equivalently the weighting. Other ways of decreasing the variable N are also possible and within embodiments of the present technology.

Block 805 is performed if the message was determined to be received in the presence of excessive noise, and/or if there was the presence of excessive noise in the channel over which messages can be received. This block increases the value of the variable "N", which as noted above essentially represents a time average of the number of messages received in the presence of excessive noise and/or a time average of excessive noise being present in the channel, and more generally is indicative of the extent of messages received in the presence of excessive noise over time and/or indicative of the extent that excessive noise was present over time in the channel. In an embodiment, the single-pole low pass filter algorithm N:=(1−1/a)*N+1/a is used to increase the value of "N" at Block 805. Other ways of increasing the variable N are also possible and within embodiments of the present technology.

Block 806 checks to see if N exceeds a first threshold parameter "tha". Exceeding the first threshold parameter tha is an indication that the device is in an electrically noisy environment. In accordance with an embodiment, the first threshold parameter tha is in the range of 0 to 1. For example, tha can be 0.6.

Block 808, which is performed if the first threshold parameter tha is exceeded, sets the device into the Noise State. This can involve changing a State Flag from 0 to 1, or vice versa, depending upon implementation.

Block 807 is normal message processing. Following normal processing, the method exits in Block 809. Normal processing of a received valid message can involve the device being responsive to the valid message, e.g., by performing pacing in response to the valid message.

The Noise path, shown at the right in FIG. 8 will now be discussed, which path is followed when the LP 102 is in its Noise State. If the device is in the Noise State, Block 810 is performed, which does the same function as Block 802. Block 811 determines whether a message was received in the absence or presence of excessive noise and/or whether there is an absence or presence of excessive noise in the channel over which messages can be received, similar to Block 803.

If the message was received in the absence of excessive noise, or if excessive noise was absent from the channel, Block 812 decreases the variable "N", which as noted above is indicative of the extent that messages were received over time in the presence of excessive noise and/or the extent that excessive noise was present in the channel over time. Again a low pass filter algorithm can be used to implement an exponentially weighted average. More specifically, a single-pole digital low pass filter algorithm $N:=(1-1/b)*N$ can be used at Block 812. Here, the time constant parameter "b" controls the rate and, in accordance with an embodiment, is different from the parameter "a" because it can be desirable to have a different timing to resume normal operation and because the update rate for this path will be less frequent. It is also possible that the parameter "b" is the same as the parameter "a". Decision Block 814 decides whether the variable N has fallen sufficiently to warrant return to the Normal State. This is performed by checking to see if the variable N is less than a second threshold parameter "thb". In accordance with an embodiment, the second threshold parameter thb is in the range of 0 to 1 and is less than the first threshold parameter tha in order to provide hysteresis. It is also possible that the second threshold parameter thb is the same as the first threshold parameter tha, but this is less preferred as it may result in constant toggling back between the Normal State and the Noise State without any hysteresis.

Block 815 performs the state change to the Normal State.

Block 813 is performed when the device is in the Noise State and the received message is received in the presence of excessive noise or when excessive noise is present in the channel over which messages can be received. This block causes the variable N to increase, indicating that the average number of invalid messages and/or the extent of noise in the channel is greater, and more generally indicatives an increase in the extent of messages received in the presence of excessive noise over time and/or an increase in the extent over time that excessive noise is present in the channel. In an embodiment, the single-pole low pass filter algorithm $N:=(1-1/b)*N+1/b$ is used to increase the value of "N" at Block 813. Other ways of updating the variable N are also possible and within embodiments of the present technology.

Block 816, "Disable Receiver(s) for T seconds" is performed in the Noise State and conserves power by ensuring that the power consuming high-bandwidth receiver is put to sleep. The i2i messages will be resampled after this time T expires and/or the channel will be reexamined after this time T expires. At Block 816, both the first and second receivers 120 and 122 can be put to sleep for T seconds, or just the second receiver 122 can be put to sleep for T seconds. More generally, at Block 816 at least one of the first and second receivers is put to sleep for at least a sleep period of T seconds. The method exits through Block 817. In an electrically noisy environment, this method turns on (or more generally, awakens) the receivers every T seconds rather than continually, thus conserving battery energy. T can be within the range of 5 seconds to 600 second, e.g., 60 seconds, but is not limited thereto. In accordance with certain embodiments, T is a programmed value that is specified, e.g., by a manufacturer, clinician or physician. In accordance with other embodiments, it is possible to extend T up to a limit if messages continue to be received in the presence of excessive noise, which would afford greater power conservation at the expense of taking longer to return to normal operation. In other words, T may be selectively increased or decreased based on the results of examining received messages. The time period specified by the value T can be referred to as the sleep period, as was also the case in the embodiments described above with reference to FIGS. 6 and 7.

In the embodiments described above with reference to FIG. 8, a variable "N", which is indicative of the extent that messages were received over time in the presence of excessive noise and/or indicative of the extent that excessive noise was present over time in the channel over which messages can be received, is adjusted and used to determine when the device should be in a Normal State or a Noise State. The variable "N" can also be referred to as a Noise value indicative of the extent of messages received in the presence of excessive noise over time, and/or indicative of the extent of the presence of excessive noise over time in the channel over which messages can be received.

In alternative embodiments, described below with reference to FIG. 9, a variable "Q" that is indicative of the extent that messages were received in the absence of excessive noise over time (and/or indicative of the absence of excessive noise over time in the channel over which messages can be received) is adjusted and used to determine when the device should be in a Normal State or a Noise State. The variable "Q" can also be referred to as a Quiescent value indicative of the extent that messages were received in the absence of excessive noise over time, and/or indicative of the extent of the absence of excessive noise over time in the channel over which messages can be received.

Figure 9:
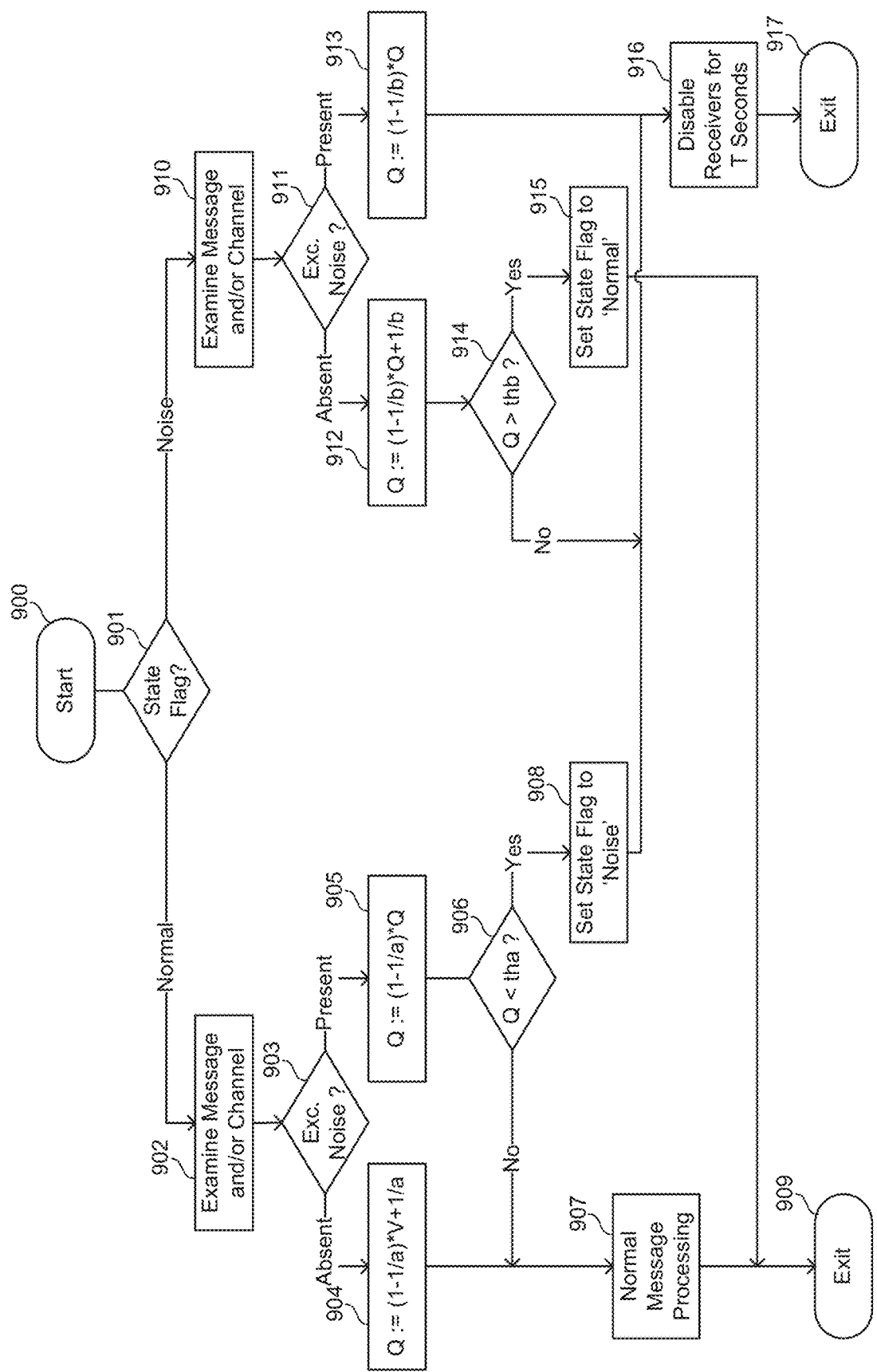

Referring to FIG. 9, Blocks 900, 902, 903, 910 and 911 are the same, respectively, as Blocks 800, 802, 803, 810 and 811 described above with reference to FIG. 8, and thus, need not be described in detail again.

Block 903, is a decision block that depends on the whether the message was received in the presence or absence for the Normal State, and/or whether there was a presence or absence of excessive noise in the channel over which messages can be received, as was Block 803.

If the message was received in the absence of excessive noise, or if there was an absence of excessive noise in the channel, Block 904 is performed. This block effectively increases the variable "Q" which essentially represents a time average of the number of messages received in the absence of excessive noise, and/or a time average of the absence of excessive noise in the channel over which messages can be received. In other words, a value of the variable "Q" is indicative of the extent of messages received in the absence of excessive over time, and/or indicative of the extent that there was an absence of excessive noise over time in the channel, as noted above. In an embodiment, the variable "Q" ranges from 0 to 1 and is calculated by a single-pole digital low pass filter algorithm $Q:=(1-1/a)*Q+1/a$. As a result, the low pass filter algorithm implements an exponentially weighted average. The time constant parameter "a" controls the rate of change or equivalently the weighting, as was the case in the embodiment of FIG. 8. Other ways of increasing the variable Q are also possible and within embodiments of the present technology.

Block 805 is performed if the message was determined to be received in the presence of excessive noise, or if it was determined that there was excessive noise in the channel over which messages can be received. This block decreases the value of the variable "Q", which as noted above essentially represents a time average of the number of messages received in the absence of excessive noise and/or a time average of the absence of excessive noise in the channel, and more generally is indicative of the extent of messages received in the absence of excessive noise over time and/or indicative of the extent that there was an absence of excessive noise over time in the channel. In an embodiment, the single-pole low pass filter algorithm Q:=(1−1/a)*Q is used to decrease the value of "Q" at Block 905. Other ways of decreasing the variable Q are also possible and within embodiments of the present technology.

Block 906 checks to see if Q is less than a first threshold parameter "tha". Being less than the first threshold parameter tha is an indication that the device is in an electrically noisy environment. In accordance with an embodiment, the first threshold parameter tha is in the range of 0 to 1. For example, tha can be 0.6.

Block 908, which is performed if Q is less than the first threshold parameter tha, sets the device into the Noise State. This can involve changing a State Flag from 0 to 1, or vice versa, depending upon implementation.

Block 907 is normal message processing. Following normal processing, the method exits in Block 909. Normal processing of a message received in the absence of excessive noise can involve the device being responsive to the message, e.g., by performing pacing in response to the valid message.

The Noise path, shown at the right in FIG. 9 will now be discussed, which path is followed when the LP 102 is in its Noise State. If the device is in the Noise State, Block 910 is performed, which does the same function as Block 902. Block 911 checks to determine whether a message was received in the presence or absence of excessive noise, and/or if there was the presence or absence of excessive noise in the channel over which messages can be received, similar to Block 903.

If the message was received in the absence of excessive noise, or if excessive noise was absent in the channel, Block 912 increases the variable "Q", which as noted above is indicative of the extent that messages were received in the absence of excessive noise over time and/or is indicative of the extent that excessive noise was absent over time in the channel over which messages can be received. Again a low pass filter algorithm can be used to implement an exponentially weighted average. More specifically, a single-pole digital low pass filter algorithm V:=(1−1/b)*V+1/b can be used at Block 912. Here, the time constant parameter "b" controls the rate and, in accordance with an embodiment, is different from the parameter "a" because it can be desirable to have a different timing to resume normal operation and because the update rate for this path will be less frequent, as was also the case in the embodiment of FIG. 8. It is also possible that the parameter "b" is the same as the parameter "a".

Decision Block 914 decides whether the variable Q has increased sufficiently to warrant return to the Normal State. This is performed by checking to see if the variable Q is greater than a second threshold parameter "thb". In accordance with an embodiment, the second threshold parameter thb is in the range of 0 to 1 and is greater than the first threshold parameter tha in order to provide hysteresis. It is also possible that the second threshold parameter thb is the same as the first threshold parameter tha, but this is less preferred as it may result in constant toggling back between the Normal State and the Noise State without any hysteresis.

Block 915 performs the state change to the Normal State.

Block 913 is performed when the device is in the Noise State and the received message was received in the presence of excessive noise, or excessive noise was present in the channel over which messages can be received. This block causes the variable Q to decrease, indicating that the average number of messages received in the absence of excessive noise is reduced or indicating that average time that excessive noise was absent from the channel is reduced, and more generally indicatives a decrease in the extent of messages received in the absence of excessive noise over time and/or indicates a decrease in the extent of the absence of excessive noise over time in the channel. In an embodiment, the single-pole low pass filter algorithm V:=(1−1/b)*V is used to decrease the value of "V" at Block 913. Other ways of updating the variable Q are also possible and within embodiments of the present technology.

Block 916 is the same as Block 916, and thus its details need not be repeated.

Figure 10:
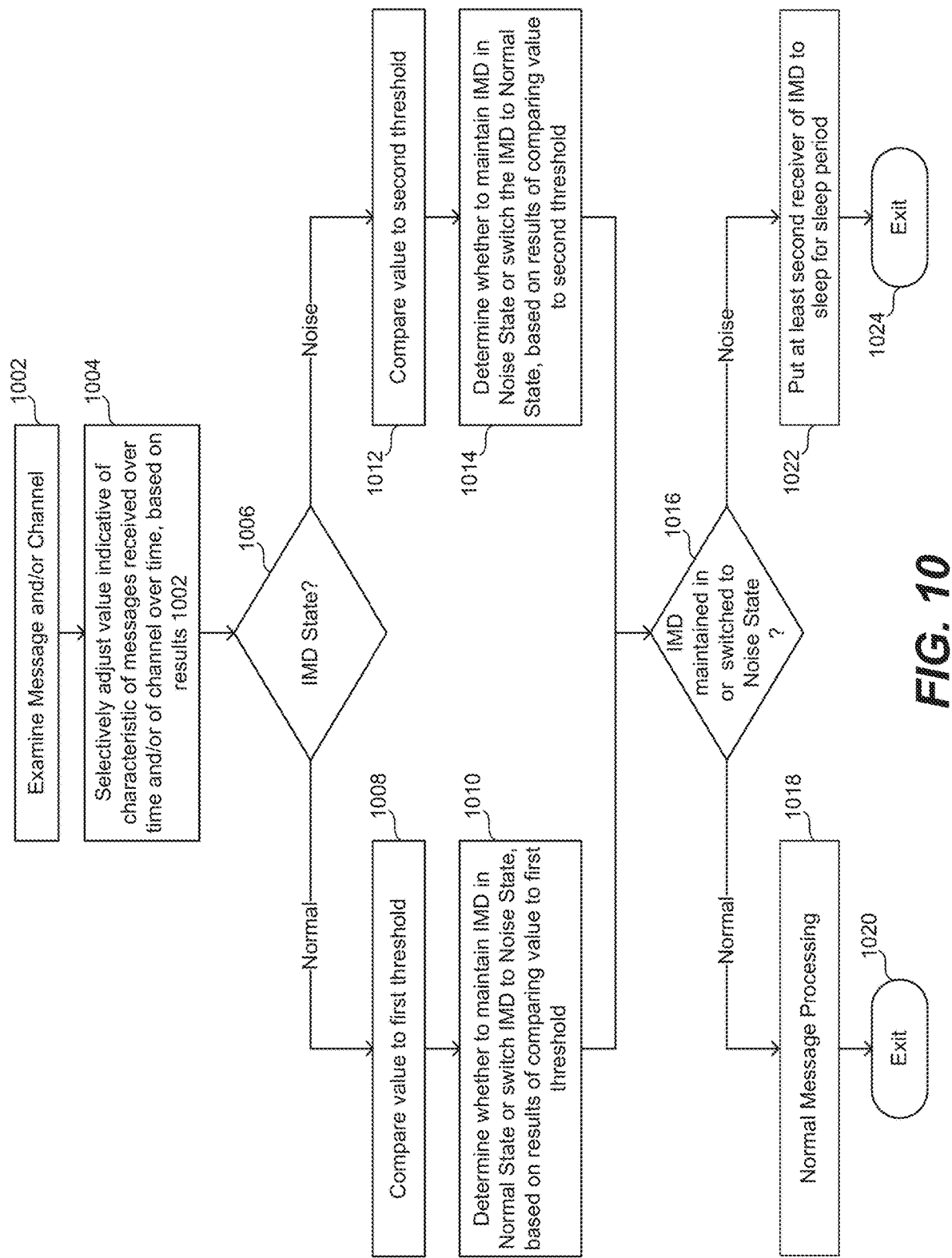
FIG. 10 is a more generic high level flow diagram that is used to more generally summarize methods according to various embodiments of the present technology that reduce how often a first receiver of a device wakes up a second receiver of the device and thereby reduces power consumed by the device.

FIG. 10 a more generic high level flow diagram that are used to more generally summarize methods according to various embodiments of the present technology that reduce how often a first receiver of a device wakes up a second receiver of the device and thereby reduces power consumed by the device. Referring to FIG. 10, Block 1002 involves examining a received message and/or a examining channel over which messages can be received, and Block 1004 involves selectively adjusting a value, indicative of a characteristic of messages received over time and/or a characteristic of the channel over time, based on results of the examining performed at Block 1002. In accordance with certain embodiments, an amount by which the value is selectively adjusted at Block 1004 can be different depending upon whether the IMD is in the Normal State or the Noise State. For example, the amount by which the value is adjusted can be greater when the IMD is in the Normal State than when it is in the Noise State, or vice versa, depending upon whether the desire is to maximize or minimize how often the IMD is in the Normal State versus the Noise State. Additionally or alternatively, the amount by which the value is selectively adjusted at Block 1004 can be different depending upon whether the value is being increased or decreased. For example, the amount by which the value is adjusted can be greater when the value is increased than the amount by which the value is adjusted when the value is decreased, or vice versa, depending upon whether the desire is to maximize or minimize how often the IMD is in the Normal State versus the Noise State. As explained above in the discussion of FIGS. 1-9, when the IMD is in the Normal State, normal pacing can occur, but the IMD will likely consume more power in the Normal State than when the IMD is in the Noise State due to the first receiver of the IMD often waking up the second receiver of the IMD. Conversely, when the IMD is in the Noise State, the IMD will likely consume less power, but may have to operate in a safe pacing mode, which is less desirable than a normal pacing mode.

In accordance with certain embodiments, prior to Block 1002 being performed, the first receiver (e.g., 120) of the IMD (e.g., LP 102 or 104) receives at least a portion of the message, and in response thereto, the first receiver (e.g., 120) wakes up the second receiver (e.g., 122) so that the second receiver (e.g., 122) can perform the examining of the received message at block 1002.

Still referring to FIG. 10, Block 1006 involves determining whether the IMD is in a Normal State or a Noise State. If the IMD is in the Normal State, then a Normal path is followed and Block 1008 involves comparing the value (as adjusted at Block 1004) to a first threshold, and Block 1010 involves determining whether to maintain the IMD in the normal state or switch the IMD to the noise state, based on results of the comparing the value to the first threshold at Block 1008. If the IMD is in the Noise State, then a Noise path is followed and Block 1012 involves comparing the value (as adjusted at Block 1004) to a second threshold, and Block 1014 involves determining whether to maintain the IMD in the noise state or switch the IMD to the normal state, based on results of the comparing the value to the second threshold at Block 1012. The first and second threshold can be the same as one another, but they are preferably different to provide for hysteresis. Block 1016 involves determining if the IMD has been one of maintained or switched to the Noise State. If the IMD has not been maintained or switched to the Noise State, and thus, is in the Normal State, then the Normal path is followed and normal message processing is performed at Block 1018 and the method is exited at Block 1020. If the IMD has been one of maintained or switched to the Noise State, then the Noise path is followed and at least the second receiver of the IMD is put to sleep for a sleep period, and the method is exited at Block 1024.

In accordance with certain embodiments, putting at least the second receiver (e.g., 122) of the IMD to sleep for the sleep period, at Block 1022, also includes putting the first receiver (e.g., 120) of the IMD to sleep for the sleep period. In accordance with certain embodiments, during the sleep period, there is no examining of any received messages. In accordance with certain embodiments, the sleep period can be selectively increased or decreased based on the results of examining the received message at Block 1002.

In accordance with certain embodiments, such as those described above with reference to FIGS. 6 and 7, the examining the received message at Block 1002 involves determining whether the received message is valid or invalid. In such embodiments, the characteristic of messages received over time can be an extent of valid or invalid messages received over time. Accordingly, at Block 1004 the selectively adjusting the value, which is indicative of the extent of valid or invalid messages received over time, can be based on results of the determining whether the received message is valid or invalid. In certain embodiments, the result of determining whether a received message is valid or invalid at Block 1002 may be indeterminate, in which case the value is not adjusted, i.e., is unchanged. In accordance with certain embodiments, Block 1018 involves processing the received message, if the received message is valid and the IMD is maintained or switched to the normal state. Conversely, the IMD may not process the received message, if the IMD is maintained or switched to the noise state. If the IMD is maintained in the Normal State, after a received message is determined to be invalid, the invalid message can either not be processed, or the invalid message can be processed but results of the processing can be ignored.

In accordance with specific embodiments, such as those specifically described above with reference to FIG. 6, the value that is selectively adjusted at Block 1004 is an invalidity value indicative of the extent of invalid messages received over time. In such embodiments, Block 1004 can involve adjusting the invalidity value, based on results of the determining whether the received message is valid or invalid, and more particularly, can include decreasing the invalidity value if the received message is valid, or increasing the invalidity value if the received message is invalid. The first and second thresholds can be the same in such embodiments, but more preferably the first threshold is greater than the second threshold so at to provide hysteresis.

In accordance with other specific embodiments, such as those specifically described above with reference to FIG. 7, the value that is selectively adjusted at Block 1004 is a validity value indicative of the extent of valid messages received over time. In such embodiments, Block 1004 can involve adjusting the validity value, based on results of the determining whether the received message is valid or invalid, and more particularly, can include increasing the validity value if the received message is valid, or decreasing the validity value if the received message is invalid. The first and second thresholds can be the same in such embodiments, but more preferably the first threshold is less than the second threshold so at to provide hysteresis.

In accordance with certain embodiments, such as those described above with reference to FIGS. 8 and 9, the examining the received message and/or the examining the channel at Block 1002 involves determining whether the received message was received in the presence or absence of excessive noise and/or determining whether there is a presence or absence of excessive noise in the channel over which messages can be received. In certain such embodiments, a characteristic of messages received over time can be an extent that excessive noise was present or absent when messages were received over time. Alternatively, or additionally, a characteristic can be an extent that excessive noise was present or absent in the channel over which messages can be received. Accordingly, Block 1004 can involve selectively adjusting the value, which is indicative of the extent that excessive noise was present or absent when messages were received over time, and/or indicative of the extent that that excessive noise was present or absent in the channel, based on results of the determining whether the received message was received in the presence or absence of excessive noise and/or results of determining whether there was the presence or absence of excessive noise in the channel over which messages can be received. As was explained above with reference to FIGS. 8 and 9, determining whether a received message was received in the presence or absence of excessive noise can involve determining whether one or more characteristics (e.g., pulse width, pulse amplitude and/or pulse interval) of the received message is/are within expected ranges, but is not limited thereto. In certain embodiments, the result of determining whether a received message was received in the presence or absence of excessive noise at Block 1002 may be indeterminate, in which case the value is not adjusted, i.e., is unchanged. It is also possible to determine the extent of the noise in a channel without examining any message. In accordance with certain embodiments, Block 1018 involves processing a received message, if the received message was received in the absence of excessive noise and the IMD is maintained or switched to the normal state. Conversely, the IMD may not process the received message, if the IMD is maintained or switched to the noise state. If the IMD is maintained in the Normal State, after a received message is determined have been received in the presence of excessive noise, the message can either not be processed, or the message can be processed but results of the processing can be ignored.

In accordance with specific embodiments, such as those described above with reference to FIG. 8, the value that is selectively adjusted at Block 1004 is a noise value indicative of the presence of excessive noise when messages were received over time and/or indicative of the presence of excessive noise over time in the channel over which messages can be received. In such embodiments, Block 1004 can involve decreasing the noise value if the received message was received in the absence of excessive noise or if there was an absence of excessive noise in the channel, or increasing the noise value if the received message was received in the presence of excessive noise or if there was the presence of excessive noise in the channel. The first and second thresholds can be the same in such embodiments, but more preferably the first threshold is greater than the second threshold so at to provide hysteresis.

In accordance with other specific embodiments, such as those described above with reference to FIG. 9, the value that is selectively adjusted at Block 1004 is a quiescent value indicative of the absence of excessive noise when messages were received over time and/or the absence of excessive noise over time in the channel. In such embodiments, Block 1004 can involve increasing the quiescent value if the received message was received in the absence of excessive noise or if there was an absence of excessive noise in the channel, or decreasing the quiescent value if the received message was received in the presence of excessive noise or if there was the presence of excessive noise in the channel. The first and second thresholds can be the same in such embodiments, but more preferably the first threshold is less than the second threshold so at to provide hysteresis.

Figure 11:
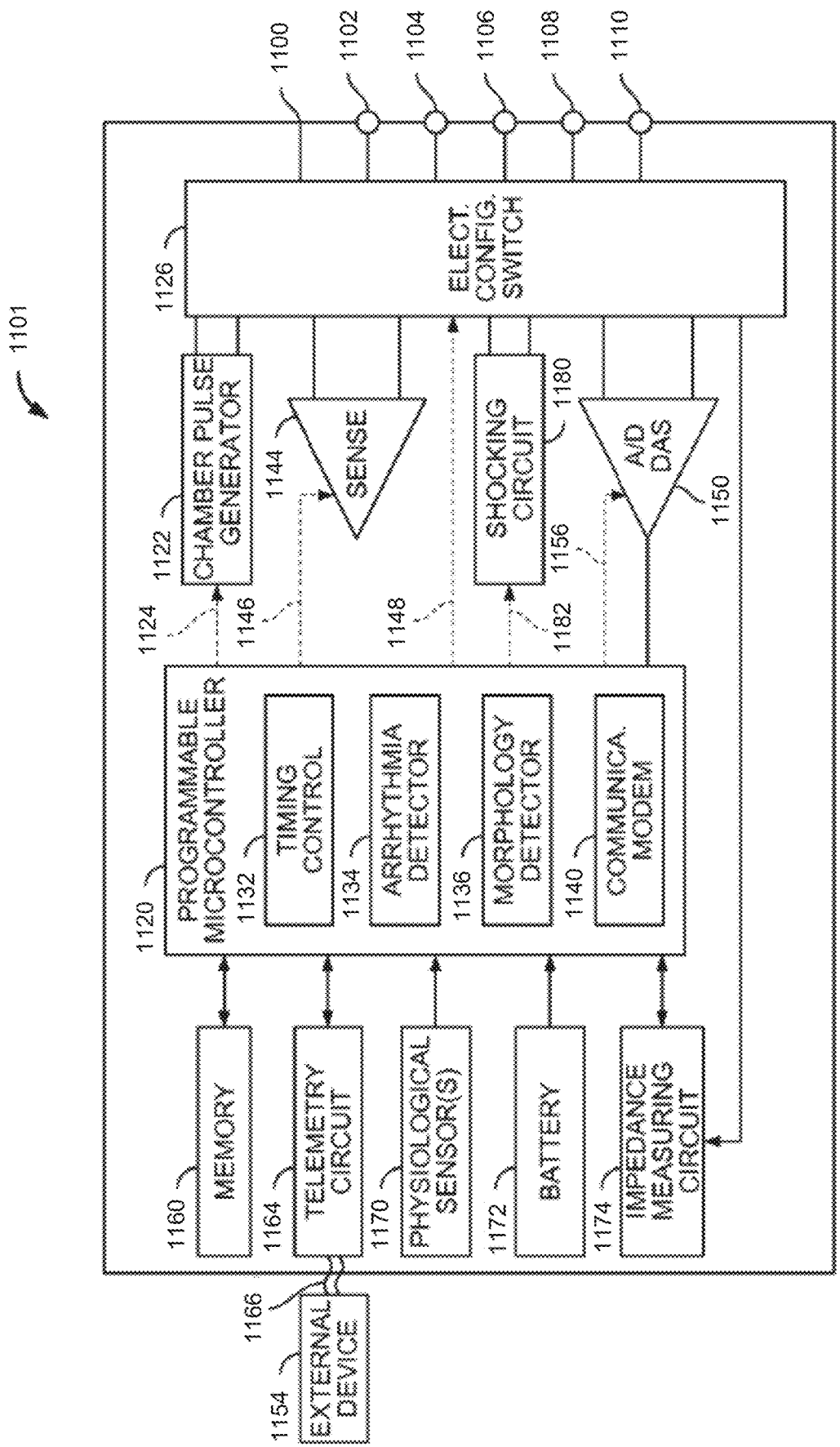
FIG. 11 shows a block diagram of one embodiment of an LP that is implanted into the patient as part of the implantable cardiac system in accordance with certain embodiments herein.

FIG. 11 shows a block diagram of one embodiment of an LP 1101 that is implanted into the patient as part of the implantable cardiac system in accordance with certain embodiments herein. LP 1101 may be implemented as a full-function biventricular pacemaker, equipped with both atrial and ventricular sensing and pacing circuitry for four chamber sensing and stimulation therapy (including both pacing and shock treatment). Optionally, LP 1101 may provide full-function cardiac resynchronization therapy. Alternatively, LP 1101 may be implemented with a reduced set of functions and components. For instance, the IMD may be implemented without ventricular sensing and pacing.

LP 1101 has a housing 1100 to hold the electronic/computing components. Housing 1100 (which is often referred to as the "can", "case", "encasing", or "case electrode") may be programmably selected to act as the return electrode for certain stimulus modes. Housing 1100 may further include a connector (not shown) with a plurality of terminals 1102, 1104, 1106, 1108, and 1110. The terminals may be connected to electrodes that are located in various locations on housing 1100 or elsewhere within and about the heart. LP 1101 includes a programmable microcontroller 1120 that controls various operations of LP 1101, including cardiac monitoring and stimulation therapy. Microcontroller 1120 includes a microprocessor (or equivalent control circuitry), RAM and/or ROM memory, logic and timing circuitry, state machine circuitry, and I/O circuitry.

LP 1101 further includes a first pulse generator 1122 that generates stimulation pulses for delivery by one or more electrodes coupled thereto. Pulse generator 1122 is controlled by microcontroller 1120 via control signal 1124. Pulse generator 1122 may be coupled to the select electrode(s) via an electrode configuration switch 1126, which includes multiple switches for connecting the desired electrodes to the appropriate I/O circuits, thereby facilitating electrode programmability. Switch 1126 is controlled by a control signal 1128 from microcontroller 1120.

In the embodiment of FIG. 11, a single pulse generator 1122 is illustrated. Optionally, the IMD may include multiple pulse generators, similar to pulse generator 1122, where each pulse generator is coupled to one or more electrodes and controlled by microcontroller 1120 to deliver select stimulus pulse(s) to the corresponding one or more electrodes.

Microcontroller 1120 is illustrated as including timing control circuitry 1132 to control the timing of the stimulation pulses (e.g., pacing rate, atrio-ventricular (AV) delay, atrial interconduction (A-A) delay, or ventricular interconduction (V-V) delay, etc.). Timing control circuitry 1132 may also be used for the timing of refractory periods, blanking intervals, noise detection windows, evoked response windows, alert intervals, marker channel timing, and so on. Microcontroller 1120 also has an arrhythmia detector 1134 for detecting arrhythmia conditions and a morphology detector 1136. Although not shown, the microcontroller 1120 may further include other dedicated circuitry and/or firmware/software components that assist in monitoring various conditions of the patient's heart and managing pacing therapies.

LP 1101 is further equipped with a communication modem (modulator/demodulator) 1140 to enable wireless communication with the remote slave pacing unit. Modem 1140 may include one or more transmitters and two or more receivers as discussed herein in connection with FIG. 1B. In one implementation, modem 1140 may use low or high frequency modulation. As one example, modem 1140 may transmit i2i messages and other signals through conductive communication between a pair of electrodes. Modem 1140 may be implemented in hardware as part of microcontroller 1120, or as software/firmware instructions programmed into and executed by microcontroller 1120. Alternatively, modem 1140 may reside separately from the microcontroller as a standalone component.

LP 1101 includes a sensing circuit 1144 selectively coupled to one or more electrodes, that perform sensing operations, through switch 1126 to detect the presence of cardiac activity in the right chambers of the heart. Sensing circuit 1144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1126 determines the sensing polarity of the cardiac signal by selectively closing the appropriate switches. In this way, the clinician may program the sensing polarity independent of the stimulation polarity.

The output of sensing circuit 1144 is connected to microcontroller 1120 which, in turn, triggers or inhibits the pulse generator 1122 in response to the presence or absence of cardiac activity. Sensing circuit 1144 receives a control signal 1146 from microcontroller 1120 for purposes of controlling the gain, threshold, polarization charge removal circuitry (not shown), and the timing of any blocking circuitry (not shown) coupled to the inputs of the sensing circuitry.

In the embodiment of FIG. 11, a single sensing circuit 1144 is illustrated. Optionally, the IMD may include multiple sensing circuits, similar to sensing circuit 1144, where each sensing circuit is coupled to one or more electrodes and controlled by microcontroller 1120 to sense electrical activity detected at the corresponding one or more electrodes.

Sensing circuit 1144 may operate in a unipolar sensing configuration or in a bipolar sensing configuration.

LP 1101 further includes an analog-to-digital (A/D) data acquisition system (DAS) 1150 coupled to one or more electrodes via switch 1126 to sample cardiac signals across any pair of desired electrodes. Data acquisition system 1150 is configured to acquire intracardiac electrogram signals, convert the raw analog data into digital data, and store the digital data for later processing and/or telemetric transmission to an external device 1154 (e.g., a programmer, local transceiver, or a diagnostic system analyzer). Data acquisition system 1150 is controlled by a control signal 1156 from the microcontroller 1120.

Microcontroller 1120 is coupled to a memory 1160 by a suitable data/address bus. The programmable operating parameters used by microcontroller 1120 are stored in memory 1160 and used to customize the operation of LP 1101 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 1101 may be non-invasively programmed into memory 1160 through a telemetry circuit 1164 in telemetric communication via communication link 1166 with external device 1154. Telemetry circuit 1164 allows intracardiac electrograms and status information relating to the operation of LP 1101 (as contained in microcontroller 1120 or memory 1160) to be sent to external device 1154 through communication link 1166.

LP 1101 can further include magnet detection circuitry (not shown), coupled to microcontroller 1120, to detect when a magnet is placed over the unit. A magnet may be used by a clinician to perform various test functions of LP 1101 and/or to signal microcontroller 1120 that external device 1154 is in place to receive or transmit data to microcontroller 1120 through telemetry circuits 1164.

LP 1101 can further include one or more physiological sensors 1170. Such sensors are commonly referred to as "rate-responsive" sensors because they are typically used to adjust pacing stimulation rates according to the exercise state of the patient. However, physiological sensor 1170 may further be used to detect changes in cardiac output, changes in the physiological condition of the heart, or diurnal changes in activity (e.g., detecting sleep and wake states). Signals generated by physiological sensors 1170 are passed to microcontroller 1120 for analysis. Microcontroller 1120 responds by adjusting the various pacing parameters (such as rate, AV Delay, V-V Delay, etc.) at which the atrial and ventricular pacing pulses are administered. While shown as being included within LP 1101, physiological sensor(s) 1170 may be external to LP 1101, yet still be implanted within or carried by the patient. Examples of physiologic sensors might include sensors that, for example, sense respiration rate, pH of blood, ventricular gradient, activity, position/posture, minute ventilation (MV), and so forth.

A battery 1172 provides operating power to all of the components in LP 1101. Battery 1172 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1172 also desirably has a predictable discharge characteristic so that elective replacement time can be detected. As one example, LP 1101 employs lithium/silver vanadium oxide batteries.

LP 1101 further includes an impedance measuring circuit 1174, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1174 is coupled to switch 1126 so that any desired electrode may be used. In this embodiment LP 1101 further includes a shocking circuit 1180 coupled to microcontroller 1120 by a data/address bus 1182.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for managing wake-up operations of first and second receivers of an implantable medical device (IMD), the method comprising:
   configuring the first receiver of the IMD to selectively wakeup the second receiver of the IMD, wherein the second receiver when awake consumes more power than the first receiver;
   receiving a message at the first receiver;
   examining the message to determine whether the message is valid or invalid;
   adjusting a value of a variable indicative of an extent of valid or invalid messages received during a time period;
   comparing the value to a threshold; and
   disabling the second receiver for a select time period based on the comparing of the value to the threshold, to avoid excessive wakeups of the second receiver in a noisy environment.

2. The method of claim 1, wherein the threshold includes first and second thresholds, the method further comprising:
   when the IMD is in a normal state, switching the IMD from the normal state to a noise state based on comparing the value to the first threshold; and
   when the IMD is in the noise state, switching the IMD to the normal state, based on comparing the value to the second threshold.

3. The method of claim 1, wherein the disabling comprising putting at least the second receiver to sleep for a sleep period.

4. The method of claim 3, wherein the putting at least the second receiver to sleep includes putting the first receiver to sleep for the sleep period.

5. The method of claim 1, wherein, during the select time period, there is no examining of any of the messages received during the time period and no actions are performed based on the messages received during the time period.

6. The method of claim 1, wherein the variable represents an average number of the valid or invalid messages received over the select time period.

7. The method of claim 1, further comprising, when the IMD is in a noise state, periodically checking for the valid messages; and when the first receiver receives the valid messages for at least a specified amount of time, switching the IMD from the noise state to a normal state.

8. The method of claim 1, wherein the IMD is a first leadless pacemaker located in a first chamber of a heart and the message received is from a second leadless pacemaker located remotely in a second chamber of the heart.

9. The method of claim 1, further comprising configuring the first and second receivers to communicate over separate first and second receive channels, respectively.

10. The method of claim 9, wherein the first and second receive channels have different corresponding first and second fundamental frequency ranges.

11. The method of claim 1, further comprising configuring the first and second receivers to operate with different first and second activation protocols, respectively.

12. The method of claim 11, wherein the first activation protocol maintains a first receive channel, through the first receiver, active for at least a portion of a time of interval while the second activation protocol maintains a second receive channel, through the second receiver, inactive.

13. A method for managing wake-up operations in connection with communication between first and second implantable medical devices (IMDs), the first IMD comprising first and second receivers, the method comprising:
   configuring the first receiver of the first IMD to selectively wakeup the second receiver of the first IMD, wherein the second receiver of the first IMD when awake consumes more power than the first receiver;
   receiving a message at the first receiver of the first IMD;
   examining the message to determine whether the message is a valid message from the second IMD;
   adjusting a value of a variable indicative of an extent of valid or invalid messaged messages received during a time period;
   comparing the value to a threshold; and
   disabling the second receiver of the first IMD for a select time period based on the comparing of the value to the threshold parameter, to avoid excessive wakeups of the second receiver of the first IMD when the first and second IMDs are operating in a noisy environment.

14. The method of claim 13, wherein the first and second IMDs represent a first leadless pacemaker located in a first chamber of a heart and a second leadless pacemaker located remotely in a second chamber of the heart.

15. The method of claim 14, further comprising operating the first leadless pacemaker as a slave IMD and the second leadless pacemaker as a master device, the second leadless pacemaker transmitting command markers in the message to direct the first leadless pacemaker to perform an action based thereon.

16. The method of claim 15, wherein the action is to deliver a pacing pulse.

17. An implantable medical device (IMD), comprising:
   first and second receivers of the IMD:
   at least one battery configured to power the first and second receivers and other electronics of the IMD; and at least one of a processor or controller;
the first receiver configured to selectively wakeup the second receiver;
the second receiver, when awake, configured to consume more power than the first receiver; and
the at least one of the processor or controller configured to:
examine a message, received by the first receiver, to determine whether the message is valid or invalid;
adjust a value of a variable indicative of an extent of valid or invalid messages messaged received during a time period;
compare the value to a threshold; and
disable tine second receiver for a select time period based on the comparison of the value to the threshold parameter, to avoid excessive wakeups of the second receiver in a noisy environment.

18. The IMD of claim 17, wherein the at least one of the processor or controller is further configured to put at least the second receiver to sleep for a sleep period during the disable.

19. The IMD of claim 18, wherein the at least one of the processor or controller is further configured to put at least the first receiver to sleep during the disable.

20. The IMD of claim 17, further comprising configuring the first and second receivers to communicate over separate first and second receive channels, respectively.

21. The IMD of claim 17, wherein an amount by which the value is adjusted is different depending upon whether the IMD is operating in a normal state or a noise state.

22. The IMD of claim 17, wherein an amount by which the value is adjusted is different depending upon whether the value is being increased or decreased.

23. The IMD of claim 17, wherein, during the select time period, the at least one of the processor or controller does not examine any of the messages received during the time period.

24. The IMD of claim 17, wherein the variable represents an average number of the valid or invalid messages received over the select time period.

25. The IMD of claim 17, wherein the at least one of the processor or controller is further configured to periodically check for the valid messages, when the IMD is in a noise state; and switch the IMD from the noise state to a normal state when the first receiver receives the valid messages for at least a specified amount of time.

26. The IMD of claim 20, wherein the first and second receive channels have different corresponding first and second fundamental frequency ranges.

27. The IMD of claim 17, further comprising configuring the first and second receivers to operate with different first and second activation protocols, respectively.

28. The IMD of claim 27, wherein the first activation protocol maintains a first receive channel, through the first receiver, active for at least a portion of a time of interval while the second activation protocol maintains a second receive channel, through the second receiver, inactive.

\* \* \* \* \*